US007087380B2

(12) United States Patent
Griffiths et al.

(10) Patent No.: US 7,087,380 B2
(45) Date of Patent: Aug. 8, 2006

(54) FORENSIC IDENTIFICATION

(75) Inventors: Rebecca A. L. Griffiths, Birmingham (GB); Michael D. Barber, Birmingham (GB); Peter E. Johnson, Birmingham (GB); Sharon M. Gillbard, Birmingham (GB); Marc D. Haywood, Birmingham (GB); Carolyn D. Smith, Birmingham (GB); Jennifer A. Arnold, Athens (GR); Trudy Burke, Birmingham (GB); Andrew J. Urquhart, Birmingham (GB); Peter P. Gill, Birmingham (GB)

(73) Assignee: The Secretary of State of the Home Department, Birmingham (GB)

( * ) Notice: Subject to any disclaimer, the term of this patent is extended or adjusted under 35 U.S.C. 154(b) by 44 days.

(21) Appl. No.: 09/910,183

(22) Filed: Jul. 20, 2001

(65) Prior Publication Data
US 2003/0175701 A1 Sep. 18, 2003

Related U.S. Application Data

(63) Continuation of application No. 09/706,525, filed on Nov. 3, 2000, now abandoned, which is a continuation of application No. 09/498,567, filed on Feb. 4, 2000, now abandoned, which is a continuation of application No. 09/107,029, filed on Jun. 29, 1998, now abandoned.

(30) Foreign Application Priority Data
Jun. 28, 1997 (GB) .................................. 9713597.4

(51) Int. Cl.
C12Q 1/68 (2006.01)
C07H 21/02 (2006.01)
C07H 21/04 (2006.01)
(52) U.S. Cl. .................. 435/6; 536/23.1; 536/24.3
(58) Field of Classification Search ............... 435/6, 435/91.2; 536/23.1, 24.3
See application file for complete search history.

(56) References Cited
U.S. PATENT DOCUMENTS
5,599,666 A * 2/1997 Schumm et al.

OTHER PUBLICATIONS

Barber et al., Intl. J. of Legal Medicine 109 : 62-65 (1996).*
Budowle et al., Am J. of Human Genetics 48 : 137-144 (1991).*
Edwards et al., Am J. of Human Genetics 49 : 746-756 (1991).*
Kimpton et al., Electrophoresis 17 : 1283-1293 (1996).*
Sharma et al. Human Molecular Genetics 1(1) : 67 (1992).*
Sullivan et al., BioTechniques 15 (4) : 636-641 (1993).*
A. Moller, et al., *Different types of structural variation in STRs: HumFES/FPS, HumVWA and HumD21S11*, International Journal of Legal Medicine, vol. 106, 1994, pp. 319-323.
Christoph Puers et al., *Identification of Repeat Sequence Heterogeneity at the Polymorphic Short Tandem Repeat Locus HUMTH01[AATG]$_n$ and Reassignment of Alleles in Population Analysis by Using a Locus-specific Allelic Ladder*, American Journal Human Genetics, 53, 1993, pp. 953-958.
Colin Kimpton et al., *Report on the second EDNAP collaborative STR exercise*, Forensic Science International, vol. 71, 1995, pp. 137-152.
Florence Rousselet, et al., *A Pentaplex Automated Fluorescent Typing system for Forensic Identification and French Caucasian Population Data*, Journal of Forensic Sciences, vol. 42, No. 3, May 1997, pp. 500-503.
R.A.L. Griffiths, et al., *New reference allelic Ladders to improve allelic designation in a multiplex STR system*, International Journal of Legal Medicine, vol. 111, 1998. pp. 267-272.
D.J. Mancuso, et al., *Human von Willebrnad Factor Gene, Exon 39, 40, 31, and 42 and Alu repetitive element*, NCBI; Jan. 14, 1995, retrieved from http://www.ncbi.nlm.nih.gov, database accession No. M25858, XP002213448.
P. Gill, et al., *A new method of STR interpretation using inferential logic—development of a criminal intelligence database*, International Journal of Legal Medicine, vol. 109, 1996, pp. 14-22.

* cited by examiner

Primary Examiner—Ethan Whisenant
(74) Attorney, Agent, or Firm—Workman Nydegger

(57) ABSTRACT

The invention provides allelic ladder mixtures and individual alleles suitable for use in such mixtures. The allelic ladder mixtures give improved identification and distinguishing capabilities, particularly suitable in forensic investigations.

26 Claims, 6 Drawing Sheets

| Loci | Allelic Designation | Size (bp) | Loci | Allelic Designation | Size (bp) | Loci | Allelic Designation n | Size (bp) | Loci | Allelic Designation n | Size (bp) |
|---|---|---|---|---|---|---|---|---|---|---|---|
| TH01 | 4 | 150 | D8 | 7 | 157 | D18 | 8 | 266 | FGA (LMW) | 16.1 | 173 |
|  | 5 | 154 |  | 8 | 161 |  | 9 | 270 |  | 17 | 176 |
|  | 6 | 158 |  | 9 | 165 |  | 10 | 274 |  | 18 | 180 |
|  | 7 | 162 |  | 10 | 169 |  | 11 | 278 |  | 19 | 184 |
|  | 8 | 166 |  | 11 | 173 |  | 12 | 282 |  | 20 | 188 |
|  | 9 | 170 |  | 12 | 177 |  | 13 | 286 |  | 21 | 192 |
|  | 9.3 | 173 |  | 13 | 181 |  | 14 | 290 |  | 22 | 196 |
|  | 10 | 174 |  | 14 | 185 |  | 15 | 294 |  | 23 | 200 |
|  | 11 | 178 |  | 15 | 189 |  | 16 | 298 |  | 24 | 204 |
|  | 13.3 | 189 |  | 16 | 193 |  | 17 | 302 |  | 25 | 208 |
| D21 | 53 | 203 |  | 17 | 197 |  | 18 | 306 |  | 26 | 212 |
|  | 54 | 205 |  | 18 | 201 |  | 19 | 310 |  | 27 | 216 |
|  | 56 | 209 |  | 19 | 205 |  | 20 | 314 |  | 28 | 220 |
|  | 57 | 211 | VWA | 10 | 122 |  | 21 | 318 |  | 29 | 224 |
|  | 59 | 215 |  | 11 | 126 |  | 22 | 322 |  | 30 | 228 |
|  | 61 | 219 |  | 12 | 130 |  | 23 | 326 |  | 30.2 | 230 |
|  | 63 | 223 |  | 13 | 134 |  | 24 | 330 |  | 31.2 | 234 |
|  | 65 | 227 |  | 14 | 138 |  | 25 | 334 |  | 32.2 | 238 |
|  | 67 | 231 |  | 15 | 142 |  | 26 | 338 |  | 33.2 | 242 |
|  | 68 | 233 |  | 16 | 146 |  | 27 | 342 |  | 34.2 | 246 |
|  | 70 | 237 |  | 17 | 150 | AMELO | X | 105 |  | 42.2 | 278 |
|  | 72 | 241 |  | 18 | 154 |  | Y | 111 |  | 42.3 | 282 |
|  | 74 | 245 |  | 19 | 158 |  |  |  |  | 44.2 | 286 |
|  | 75 | 247 |  | 20 | 162 |  |  |  |  | 45.2 | 290 |
|  | 77 | 251 |  | 21 | 166 |  |  |  |  | 46.2 | 294 |
|  | 79 | 255 |  |  |  |  |  |  |  | 47.2 | 298 |
|  | 81 | 259 |  |  |  |  |  |  |  | 48.2 | 302 |
|  |  |  |  |  |  |  |  |  |  | 50.2 | 310 |

*FIG. 1*

HUMVWAF31/A sequences                                               FIG. 3A
10    TCTA TCTG TCTA (TCTG)$_4$ (TCTA)$_3$
12    TCTA (TCTG)$_4$ (TCTA)$_7$
13    (TCTA)$_2$ (TCTG)$_4$ (TCTA)$_3$ TCCA (TCTA)$_3$ (TCCA)$_3$ T
(Note also that the 13 allele has an atypical 3' flanking sequence (highlighted). The usual sequence is TCCA TCTA T.)

HUMTH01 sequences                                                   FIG. 3B
13.3  (TCAT)$_4$ CAT (TCAT)$_7$ TCGT$^{12th}$ TCAT D8S1179 sequences                                                   FIG. 3C
7     (TCTA)$_8$;
19    (TCTA)$_2$ TCTG (TCTA)$_{16}$ HUMFIBRA(FGA) Repeat Sequences                                      FIG. 3D
16.1  (TTTC)$_3$ TTTT TTCT (CTTT)$_6$ T (CTTT)$_3$ CTCC (TTCC)$_2$
27    (TTTC)$_3$ TTTT TTCT (CTTT)$_{13}$ CCTT (CTTT)$_5$ CTCC (TTCC)$_2$
30    (TTTC)$_3$ TTTT TTCT (CTTT)$_{16}$ CCTT (CTTT)$_5$ CTCC (TTCC)$_2$
31.2  (TTTC)$_4$ TTTT TT (CTTT)$_{15}$ (CTTC)$_3$ (CTTT)$_3$ CTCC (TTCC)$_4$
32.2  (TTTC)$_4$ TTTT TT (CTTT)$_{16}$ (CTTC)$_3$ (CTTT)$_3$ CTCC (TTCC)$_4$
33.2  (TTTC)$_4$ TTTT TT (CTTT)$_{17}$ (CTTC)$_3$ (CTTT)$_3$ CTCC (TTCC)$_4$
42.2  (TTTC)$_4$ TTTT TT (CTTT)$_8$ (CTGT)$_4$ (CTTT)$_{13}$ (CTTC)$_4$ (CTTT)$_3$ CTCC (TTCC)$_4$
43.2  (TTTC)$_4$ TTTT TT (CTTT)$_8$ (CTGT)$_5$ (CTTT)$_{13}$ (CTTC)$_4$ (CTTT)$_3$ CTCC (TTCC)$_4$
44.2  (TTTC)$_4$ TTTT TT (CTTT)$_{11}$ (CTGT)$_3$ (CTTT)$_{14}$ (CTTC)$_3$ (CTTT)$_3$ CTCC (TTCC)$_4$
45.2  (TTTC)$_4$ TTTT TT (CTTT)$_{10}$ (CTGT)$_5$ (CTTT)$_{13}$ (CTTC)$_4$ (CTTT)$_3$ CTCC (TTCC)$_4$
47.2  (TTTC)$_4$ TTTT TT (CTTT)$_{12}$ (CTGT)$_5$ (CTTT)$_{14}$ (CTTC)$_3$ (CTTT)$_3$ CTCC (TTCC)$_4$
48.2  (TTTC)$_4$ TTTT TT (CTTT)$_{14}$ (CTGT)$_3$ (CTTT)$_{14}$ (CTTC)$_4$ (CTTT)$_3$ CTCC (TTCC)$_4$ D21S11 alleles                                              FIG. 3E 53    (TCTA)$_4$ (TCTG)$_6$ (TCTA)$_3$ TA(TCTA)$_3$ TCA (TCTA)$_2$ TCCATA
(TCTA)$_6$ TCGTCT
54    (TCTA)$_5$ (TCTG)$_6$ (TCTA)$_3$ TCA (TCTA)$_2$ TCCATA (TCTA)$_9$ TCGTCT
56    (TCTA)$_5$ (TCTG)$_6$ (TCTA)$_3$ TCA (TCTA)$_2$ TCCATA (TCTA)$_{10}$ TCGTCT
57    (TCTA)$_4$ (TCTG)$_6$ (TCTA)$_3$ TA (TCTA)$_3$ TCA (TCTA)$_2$ TCCATA
(TCTA)$_8$ TCGTCT
59    (TCTA)$_5$ (TCTG)$_5$ (TCTA)$_3$ TA (TCTA)$_3$ TCA (TCTA)$_2$ TCCATA
(TCTA)$_9$ TCGTCT
61    (TCTA)$_4$ (TCTG)$_6$ (TCTA)$_3$ TA (TCTA)$_3$ TCA (TCTA)$_2$ TCCATA
(TCTA)$_{10}$ TCGTCT
63    (TCTA)$_4$ (TCTG)$_6$ (TCTA)$_3$ TA (TCTA)$_3$ TCA (TCTA)$_2$ TCCATA
(TCTA)$_{11}$ TCGTCT
65    (TCTA)$_6$ (TCTG)$_5$ (TCTA)$_3$ TA (TCTA)$_3$ TCA (TCTA)$_2$ TCCATA
(TCTA)$_{11}$ TCGTCT
67    (TCTA)$_5$ (TCTG)$_6$ (TCTA)$_3$ TA (TCTA)$_3$ TCA (TCTA)$_2$ TCCATA
(TCTA)$_{12}$ TCGTCT
68    (TCTA)$_5$ (TCTG)$_6$ (TCTA)$_3$ TA (TCTA)$_3$ TCA (TCTA)$_2$ TCCATA
(TCTA)$_{11}$ TA TCTA TCGTCT
70    (TCTA)$_5$ (TCTG)$_6$ (TCTA)$_3$ TA (TCTA)$_3$ TCA (TCTA)$_2$ TCCATA
(TCTA)$_{12}$ TA TCTA TCGTCT
72    (TCTA)$_5$ (TCTG)$_6$ (TCTA)$_3$ TA (TCTA)$_3$ TCA (TCTA)$_2$ TCCATA
(TCTA)$_{13}$ TA TCTA TCGTCT
74    (TCTA)$_5$ (TCTG)$_6$ (TCTA)$_3$ TA (TCTA)$_3$ TCA (TCTA)$_2$ TCCATA
(TCTA)$_{14}$ TATCTA TCGTCT
75    (TCTA)$_{10}$ (TCTG)$_5$ (TCTA)$_3$ TA (TCTA)$_3$ TCA (TCTA)$_2$ TCCATA
(TCTA)$_{12}$ TCGTCT
77    (TCTA)$_{11}$ (TCTG)$_5$ (TCTA)$_3$ TA (TCTA)$_3$ TCA (TCTA)$_2$ TCCATA
(TCTA)$_{12}$ TCGTCT
79    (TCTA)$_{11}$ (TCTG)$_5$ (TCTA)$_3$ TA (TCTA)$_3$ TCA (TCTA)$_2$ TCCATA
(TCTA)$_{13}$ TCGTCT
81    (TCTA)$_{13}$ (TCTG)$_5$ (TCTA)$_3$ TA (TCTA)$_3$ TCA (TCTA)$_2$ TCCATA
(TCTA)$_{12}$ TCGTCT D18S51 sequences                                            FIG. 3F
8     (AGAA)$_8$

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Homo sapiens
      (I) ORGANELLE: Mitochondrion (xi) SEQUENCE DESCRIPTION: SEQ ID NO: 1:

TCTATCTGTC TATCTGTCTG TCTGTCTGTC TATCTATCTA    40

(2) INFORMATION FOR SEQ ID NO: 2:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Homo sapiens
      (I) ORGANELLE: Mitochondrion (xi) SEQUENCE DESCRIPTION: SEQ ID NO: 2:

TCTATCTGTC TGTCTGTCTG TCTATCTATC TATCTATCTA TCTATCTA    48

(2) INFORMATION FOR SEQ ID NO: 3:

(i) SEQUENCE CHARACTERISTICS:
      (A) LENGTH: 52 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens
    (I) ORGANELLE: Mitochondrion (xi) SEQUENCE DESCRIPTION: SEQ ID NO: 3:

TCTATCTATC TGTCTGTCTG TCTGTCTATC TATCTATCCA TCTATCTATC TA          52

(2) INFORMATION FOR SEQ ID NO: 4:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 4:

TCATTCATTC ATTCATCATT CATTCATTCA TTCATTCATT CATTCATTCG TTCAT          55

(2) INFORMATION FOR SEQ ID NO: 5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 5:

TCTATCTATC TATCTATCTA TCTATCTATC TA          32

(2) INFORMATION FOR SEQ ID NO: 6:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 6:

TCTATCTATC TGTCTATCTA TCTATCTATC TATCTATCTA TCTATCTATC TATCTATCTA      60

TCTATCTATC TATCTA      76

(2) INFORMATION FOR SEQ ID NO: 7:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 7:

TTTCTTTCTT TCTTTTTTCT CTTTCTTTCT TTCTTTCTTT TCTTTCTTTC TTTCTCCTTC      60

CTTCC      65

(2) INFORMATION FOR SEQ ID NO: 8:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 8:

TTTCTTTCTT TCTTTTTTCT CTTTCTTTCT TTCTTTCTTT CTTTCTTTCT TTCTTTCTTT      60

CTTTCTTTCT TTCCTTCTTT CTTTCTTTCT TTCTTTCTCC TTCCTTCC      108

(2) INFORMATION FOR SEQ ID NO: 9:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 9:

TTTCTTTCTT TCTTTTTTCT CTTTCTTTCT TTCTTTCTTT CTTTCTTTCT TTCTTTCTTT    60

CTTTCTTTCT TTCTTTCTTT CTTTCCTTCT TTCTTTCTTT CTTTCTTTCT CCTTCCTTCC    120

(2) INFORMATION FOR SEQ ID NO: 10:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 10:

TTTCTTTCTT TCTTTCTTTT TTCTTTCTTT CTTTCTTTCT TTCTTTCTTT CTTTCTTTCT    60

TTCTTTCTTT CTTTCTTTCT TTCTTCCTTC CTTCCTTTCT TTCTTTCTCC TTCCTTCCTT    120

CCTTCC                                                                126

(2) INFORMATION FOR SEQ ID NO: 11:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 11:

TTTCTTTCTT TCTTTCTTTT TTCTTTCTTT CTTTCTTTCT TTCTTTCTTT CTTTCTTTCT    60

TTCTTTCTTT CTTTCTTTCT TTCTTTCTTC CTTCCTTCCT TTCTTTCTTT CTCCTTCCTT    120

CCTTCCTTCC                                                            130

(2) INFORMATION FOR SEQ ID NO: 12:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 12:

TTTCTTTCTT TCTTTCTTTT TTCTTTCTTT CTTTCTTTCT TTCTTTCTTT CTTTCTTTCT        60

TTCTTTCTTT CTTTCTTTCT TTCTTTCTTT CTTCCTTCCT TCCTTTCTTT CTTTCTCCTT       120

CCTTCCTTCC TTCC                                                         134

(2) INFORMATION FOR SEQ ID NO: 13:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 13:

TTTCTTTCTT TCTTTCTTTT TTCTTTCTTT CTTTCTTTCT TTCTTTCTTT CTTTCTGTCT        60

GTCTGTCTGT CTTTCTTTCT TTCTTTCTTT CTTTCTTTCT TTCTTTCTTT CTTTCTTTCT       120

TTCTTCCTTC CTTCCTTCCT TTCTTTCTTT CTCCTTCCTT CCTTCCTTCC                  170

(2) INFORMATION FOR SEQ ID NO: 14:

(i) SEQUENCE CHARACTERISTICS:
        (A) LENGTH: 174 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 14:

TTTCTTTCTT TCTTTCTTTT TTCTTTCTTT CTTTCTTTCT TTCTTTCTTT CTTTCTGTCT        60

GTCTGTCTGT CTGTCTTTCT TTCTTTCTTT CTTTCTTTCT TTCTTTCTTT CTTTCTTTCT       120

TTCTTTCTTC CTTCCTTCCT TCCTTTCTTT CTTTCTCCTT CCTTCCTTCC TTCC             174

(2) INFORMATION FOR SEQ ID NO: 15:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens
    (I) ORGANELLE: Mitochondrion (xi) SEQUENCE DESCRIPTION: SEQ ID NO: 15:

```
TTTCTTTCTT TCTTTCTTTT TTCTTTCTTT CTTTCTTTCT TTCTTTCTTT CTTTCTTTCT    60
TTCTTTCTGT CTGTCTGTCT TTCTTTCTTT CTTTCTTTCT TTCTTTCTTT CTTTCTTTCT   120
TTCTTTCTTT CTTTCTTCCT TCCTTCCTTT CTTTCTTTCT CCTTCCTTCC TTCCTTCC    178
```

(2) INFORMATION FOR SEQ ID NO: 16:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 16:

```
TTTCTTTCTT TCTTTCTTTT TTCTTTCTTT CTTTCTTTCT TTCTTTCTTT CTTTCTTTCT    60
TTCTGTCTGT CTGTCTGTCT GTCTTTCTTT CTTTCTTTCT TTCTTTCTTT CTTTCTTTCT   120
TTCTTTCTTT CTTTCTTCCT TCCTTCCTTC CTTTCTTTCT TTCTCCTTCC TTCCTTCCTT   180
CC                                                                  182
```

(2) INFORMATION FOR SEQ ID NO: 17:

(i) SEQUENCE CHARACTERISTICS:
        (A) LENGTH: 190 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 17:

```
TTTCTTTCTT TCTTTCTTTT TTCTTTCTTT CTTTCTTTCT TTCTTTCTTT CTTTCTTTCT    60
TTCTTTCTTT CTGTCTGTCT GTCTGTCTGT CTTTCTTTCT TTCTTTCTTT CTTTCTTTCT   120
TTCTTTCTTT CTTTCTTTCT TTCTTTCTTC CTTCCTTCCT TTCTTTCTTT CTCCTTCCTT   180
CCTTCCTTCC                                                          190
```

(2) INFORMATION FOR SEQ ID NO: 18:

(i) SEQUENCE CHARACTERISTICS:
        (A) LENGTH: 194 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens
    (I) ORGANELLE: Mitochondrion (xi) SEQUENCE DESCRIPTION: SEQ ID NO: 18:

```
TTTCTTTCTT TCTTTCTTTT TTCTTTCTTT CTTTCTTTCT TTCTTTCTTT CTTTCTTTCT      60

TTCTTTCTTT CTTTCTTTCT GTCTGTCTGT CTTTCTTTCT TTCTTTCTTT CTTTCTTTCT     120

TTCTTTCTTT CTTTCTTTCT TTCTTTCTTC CTTCCTTCCT TCCTTTCTTT CTTTCTCCTT     180

CCTTCCTTCC TTCC                                                       194
```

(2) INFORMATION FOR SEQ ID NO: 19:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 19:

```
TCTATCTATC TATCTATCTG TCTGTCTGTC TGTCTGTCTG TCTATCTATC TATATCTATC      60

TATCTATCAT CTATCTATCC ATATCTATCT ATCTATCTAT CTATCTATCG TCT            113
```

(2) INFORMATION FOR SEQ ID NO: 20:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 20:

```
TCTATCTATC TATCTATCTA TCTGTCTGTC TGTCTGTCTG TCTGTCTATC TATCTATCAT      60

CTATCTATCC ATATCTATCT ATCTATCTAT CTATCTATCT ATCTATCTAT CGTCT          115
```

(2) INFORMATION FOR SEQ ID NO: 21:

(i) SEQUENCE CHARACTERISTICS:
        (A) LENGTH: 119 base pairs
        (B) TYPE: nucleic acid
        (C) STRANDEDNESS: single
        (D) TOPOLOGY: linear

```
        (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens
             (I) ORGANELLE: Mitochondrion (xi) SEQUENCE DESCRIPTION: SEQ ID NO: 21:

TCTATCTATC TATCTATCTA TCTGTCTGTC TGTCTGTCTG TCTGTCTATC TATCTATCAT     60

CTATCTATCC ATATCTATCT ATCTATCTAT CTATCTATCT ATCTATCTAT CTATCGTCT    119

(2) INFORMATION FOR SEQ ID NO: 22:

(i) SEQUENCE CHARACTERISTICS:
             (A) LENGTH: 121 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens
             (I) ORGANELLE: Mitochondrion (xi) SEQUENCE DESCRIPTION: SEQ ID NO: 22:

TCTATCTATC TATCTATCTG TCTGTCTGTC TGTCTGTCTG TCTATCTATC TATATCTATC     60

TATCTATCAT CTATCTATCC ATATCTATCT ATCTATCTAT CTATCTATCT ATCTATCGTC    120

T                                                                   121

(2) INFORMATION FOR SEQ ID NO: 23:

(i) SEQUENCE CHARACTERISTICS:
             (A) LENGTH: 125 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens
             (I) ORGANELLE: Mitochondrion (xi) SEQUENCE DESCRIPTION: SEQ ID NO: 23:

TCTATCTATC TATCTATCTA TCTGTCTGTC TGTCTGTCTG TCTATCTATC TATATCTATC     60

TATCTATCAT CTATCTATCC ATATCTATCT ATCTATCTAT CTATCTATCT ATCTATCTAT    120

CGTCT                                                               125

(2) INFORMATION FOR SEQ ID NO: 24:

(i) SEQUENCE CHARACTERISTICS:
             (A) LENGTH: 129 base pairs
             (B) TYPE: nucleic acid
             (C) STRANDEDNESS: single
             (D) TOPOLOGY: linear
```

(ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens
            (I) ORGANELLE: Mitochondrion (xi) SEQUENCE DESCRIPTION: SEQ ID NO: 24:

TCTATCTATC TATCTATCTG TCTGTCTGTC TGTCTGTCTG TCTATCTATC TATATCTATC    60

TATCTATCAT CTATCTATCC ATATCTATCT ATCTATCTAT CTATCTATCT ATCTATCTAT   120

CTATCGTCT                                                          129

(2) INFORMATION FOR SEQ ID NO: 25:

(i) SEQUENCE CHARACTERISTICS:
            (A) LENGTH: 133 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens
            (I) ORGANELLE: Mitochondrion (xi) SEQUENCE DESCRIPTION: SEQ ID NO: 25:

TCTATCTATC TATCTATCTG TCTGTCTGTC TGTCTGTCTG TCTATCTATC TATATCTATC    60

TATCTATCAT CTATCTATCC ATATCTATCT ATCTATCTAT CTATCTATCT ATCTATCTAT   120

CTATCTATCG TCT                                                     133

(2) INFORMATION FOR SEQ ID NO: 26:

(i) SEQUENCE CHARACTERISTICS:
            (A) LENGTH: 137 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens
            (I) ORGANELLE: Mitochondrion (xi) SEQUENCE DESCRIPTION: SEQ ID NO: 26:

TCTATCTATC TATCTATCTA TCTATCTGTC TGTCTGTCTG TCTGTCTATC TATCTATATC    60

TATCTATCTA TCATCTATCT ATCCATATCT ATCTATCTAT CTATCTATCT ATCTATCTAT   120

CTATCTATCT ATCGTCT                                                 137

(2) INFORMATION FOR SEQ ID NO: 27:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 27:

```
TCTATCTATC TATCTATCTA TCTGTCTGTC TGTCTGTCTG TCTGTCTATC TATCTATATC    60

TATCTATCTA TCATCTATCT ATCCATATCT ATCTATCTAT CTATCTATCT ATCTATCTAT   120

CTATCTATCT ATCTATCGTC T                                             141
```

(2) INFORMATION FOR SEQ ID NO: 28:

(i) SEQUENCE CHARACTERISTICS:
        (A) LENGTH: 143 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 28:

```
TCTATCTATC TATCTATCTA TCTGTCTGTC TGTCTGTCTG TCTGTCTATC TATCTATATC    60

TATCTATCTA TCATCTATCT ATCCATATCT ATCTATCTAT CTATCTATCT ATCTATCTAT   120

CTATCTATCT ATATCTATCG TCT                                           143
```

(2) INFORMATION FOR SEQ ID NO: 29:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 29:

```
TCTATCTATC TATCTATCTA TCTGTCTGTC TGTCTGTCTG TCTGTCTATC TATCTATATC    60

TATCTATCTA TCATCTATCT ATCCATATCT ATCTATCTAT CTATCTATCT ATCTATCTAT   120

CTATCTATCT ATCTATATCT ATCGTCT                                       147
```

(2) INFORMATION FOR SEQ ID NO: 30:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 30:

```
TCTATCTATC TATCTATCTA TCTGTCTGTC TGTCTGTCTG TCTGTCTATC TATCTATATC    60

TATCTATCTA TCATCTATCT ATCCATATCT ATCTATCTAT CTATCTATCT ATCTATCTAT   120

CTATCTATCT ATCTATCTAT ATCTATCGTC T                                  151
```

(2) INFORMATION FOR SEQ ID NO: 31:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 31:

```
TCTATCTATC TATCTATCTA TCTGTCTGTC TGTCTGTCTG TCTGTCTATC TATCTATATC    60

TATCTATCTA TCATCTATCT ATCCATATCT ATCTATCTAT CTATCTATCT ATCTATCTAT   120

CTATCTATCT ATCTATCTAT CTATATCTAT CGTCT                              155
```

(2) INFORMATION FOR SEQ ID NO: 32:

(i) SEQUENCE CHARACTERISTICS:
        (A) LENGTH: 157 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 32:

```
TCTATCTATC TATCTATCTA TCTATCTATC TATCTATCTA TCTGTCTGTC TGTCTGTCTG    60

TCTATCTATC TATATCTATC TATCTATCAT CTATCTATCC ATATCTATCT ATCTATCTAT   120

CTATCTATCT ATCTATCTAT CTATCTATCT ATCGTCT                            157
```

(2) INFORMATION FOR SEQ ID NO: 33:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 33:

TCTATCTATC TATCTATCTA TCTATCTATC TATCTATCTA TCTATCTGTC TGTCTGTCTG    60

TCTGTCTATC TATCTATATC TATCTATCTA TCATCTATCT ATCCATATCT ATCTATCTAT   120

CTATCTATCT ATCTATCTAT CTATCTATCT ATCTATCGTC T                        161

(2) INFORMATION FOR SEQ ID NO: 34:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 34:

TCTATCTATC TATCTATCTA TCTATCTATC TATCTATCTA TCTATCTGTC TGTCTGTCTG    60

TCTGTCTATC TATCTATATC TATCTATCTA TCATCTATCT ATCCATATCT ATCTATCTAT   120

CTATCTATCT ATCTATCTAT CTATCTATCT ATCTATCTAT CGTCT                   165

(2) INFORMATION FOR SEQ ID NO: 35:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 35:

TCTATCTATC TATCTATCTA TCTATCTATC TATCTATCTA TCTATCTATC TATCTGTCTG    60

TCTGTCGTC TGTCTATCTA TCTATATCTA TCTATCTATC ATCTATCTAT CCATATCTAT    120

CTATCTATCT ATCTATCTAT CTATCTATCT ATCTATCTAT CTATCGTCT               169

(2) INFORMATION FOR SEQ ID NO: 36:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 36:

AGAAAGAAAG AAAGAAAGAA AGAAAGAAAG AA    32

FORENSIC IDENTIFICATION

This application is a continuation of U.S. patent application Ser. No. 09/706,525, filed Nov. 3, 2000, now abandoned, which is a continuation of U.S. patent application Ser. No. 09/498,567, filed Feb. 4, 2000, abandoned, which is a continuation of U.S. patent application Ser. No. 09/107,029, filed Jun. 29, 1998, abandoned, which claims priority to United Kingdom Application No. 9713597.4, filed Jun. 28, 1997, which for purposes of disclosure are incorporated herein by specific reference.

The present invention is concerned with improvements in and relating to forensic identification, particularly where based on DNA profiling.

DNA profiling offers a versatile identification technique for a wide variety of applications including, anthropological, paternity and other forensic environments. The use of such profiling is significant in determining links, or their absence, between samples. Such samples might include those taken from known individuals and/or those taken from the scene of or linked to a crime.

DNA profiling based on the use of short tandem repeats (STR) or micro satellite loci is used in such applications. STR's are a class of polymorphic markers which consist of simple tandomly repeated sequences of between 1 and 6 base pairs in length. STR's in the non-coding part of the genome are generally considered.

In the human genome STR's occur every 6 to 10 kilo bases along the DNA. The length, however, varies greatly between individuals due to mutation and provides identifying characteristics as a result.

A variety of DNA profiling systems exist, including single locus analysis and multiple locus analysis where a number of STR loci are simultaneously amplified.

In analysing the results from an unknown sample it is generally considered against a ladder marker consisting of alleles derived from actual samples. The allelic ladder provides a reference point and allows correspondence of alleles to be identified clearly.

The present invention provides new alleles and new ladders incorporating them for a variety of loci. The present invention offers an improved range and coverage of markers as a result. The ladders include a number of rare alleles offering improved identification of the alleles in an unknown sample.

According to a first aspect of the invention we provide an allelic ladder mixture comprising one or more of the following allelic ladders:

i) an allelic ladder for locus HUMVWFA31/A comprising one or more of alleles comprising or consisting of sequences:—
TCTA TCTG TCTA $(TCTG)_4$ $(TCTA)_3$;
TCTA $(TCTG)_4$ $(TCTA)_7$; or
$(TCTA)_2$ $(TCTG)_4$ $(TCTA)_3$ TCCA $(TCTA)_3$ or at least 75% homologous thereto;

ii) an allelic ladder for locus HUMTHO1 comprising or consisting of sequence:—
$(TCAT)_4$ CAT $(TCAT)_7$ TCGT TCAT; or at least 75% homologous thereto;

iii) an allelic ladder for locus D8S1179 comprising one or more of alleles:
$(TCTA)_8$;
$(TCTA)_2$ $TCTG(TCTA)_{16}$ or at least 75% homologous thereto;

iv) an allelic ladder for locus HUMFIBRA/FGA comprising one or more of alleles comprising or consisting of the sequences:

$(TTTC)_3$ TTTT TTCT $(CTTT)_5$ T $(CTTT)_3$ CTCC $(TTCC)_2$;
$(TTTC)_3$ TTTT TTCT $(CTTT)_{13}$ CCTT $(CTTT)_5$ CTCC $(TTCC)_2$;
$(TTTC)_3$ TTTT TTCT $(CTTT)_{16}$ CCTT $(CTTT)_5$ CTCC $(TTCC)_2$;
$(TTTC)_4$ TTTT TT $(CTTT)_{15}$ $(CTTC)_3$ $(CTTT)_3$ CTCC $(TTCC)_4$;
$(TTTC)_4$ TTTT TT $(CTTT)_{16}$ $(CTTC)_3$ $(CTTT)_3$ CTCC $(TTCC)_4$;
$(TTTC)_4$ TTTT TT $(CTTT)_{17}$ $(CTTC)_3$ $(CTTT)_3$ CTCC $(TTCC)_4$;
$(TTTC)_4$ TTTT TT $(CTTT)_8$ $(CTGT)_4$ $(CTTT)_{13}$ $(CTTC)_4$ $(CTTT)_3$ CTCC $(TTCC)_4$;
$(TTTC)_4$ TTTT TT $(CTTT)_8$ $(CTGT)_5$ $(CTTT)_{13}$ $(CTTC)_4$ $(CTTT)_3$ CTCC $(TTCC)_4$;
$(TTTC)_4$ TTTT TT $(CTTT)_{11}$ $(CTGT)_3$ $(CTTT)_{14}$ $(CTTC)_3$ $(CTTT)_3$ CTCC $(TTCC)_4$;
$(TTTC)_4$ TTTT TT $(CTTT)_{10}$ $(CTGT)_5$ $(CTTT)_{13}$ $(CTTC)_4$ $(CTTT)_3$ CTCC $(TTCC)_4$;
$(TTTC)_4$ TTTT TT $(CTTT)_{12}$ $(CTGT)_5$ $(CTTT)_{14}$ $(CTTC)_3$ $(CTTT)_3$ CTCC $(TTCC)_4$; or
$(TTTC)_4$ TTTT TT $(CTTT)_{14}$ $(CTGT)_3$ $(CTTT)_{14}$ $(CTTC)_4$ $(CTTT)_3$ CTCC $(TTCC)_4$; or at least 75% homologous thereto;

v) an allellic ladder for locus D21S11 comprising one or more of alleles comprising or consisting of sequences:
$(TCTA)_4$ $(TCTG)_6$ $(TCTA)_3$ TA$(TCTA)_3$ TCA $(TCTA)_2$ TCCATA $(TCTA)_6$ TCGTCT;
$(TCTA)_5$ $(TCTG)_6$ $(TCTA)_3$ TCA $(TCTA)_2$ TCCATA $(TCTA)_9$ TCGTCT;
$(TCTA)_5$ $(TCTG)_6$ $(TCTA)_3$ TCA $(TCTA)_2$ TCCATA $(TCTA)_{10}$ TCGTCT;
$(TCTA)_4$ $(TCTG)_6$ $(TCTA)_3$ TA $(TCTA)_3$ TCA $(TCTA)_2$ TCCATA $(TCTA)_8$ TCGTCT;
$(TCTA)_5$ $(TCTG)_5$ $(TCTA)_3$ TA $(TCTA)_3$ TCA $(TCTA)_2$ TCCATA $(TCTA)_9$ TCGTCT;
$(TCTA)_4$ $(TCTG)_6$ $(TCTA)_3$ TA $(TCTA)_3$ TCA $(TCTA)_2$ TCCATA $(TCTA)_{10}$ TCGTCT;
$(TCTA)_4$ $(TCTG)_6$ $(TCTA)_3$ TA $(TCTA)_3$ TCA $(TCTA)_2$ TCCATA $(TCTA)_{11}$ TCGTCT;
$(TCTA)_6$ $(TCTG)_5$ $(TCTA)_3$ TA $(TCTA)_3$ TCA $(TCTA)_2$ TCCATA $(TCTA)_{11}$ TCGTCT;
$(TCTA)_5$ $(TCTG)_6$ $(TCTA)_3$ TA $(TCTA)_3$ TCA $(TCTA)_2$ TCCATA $(TCTA)_{12}$ TCGTCT;
$(TCTA)_5$ $(TCTG)_6$ $(TCTA)_3$ TA $(TCTA)_3$ TCA $(TCTA)_2$ TCCATA $(TCTA)_{11}$ TA TCTA TCGTCT;
$(TCTA)_5$ $(TCTG)_6$ $(TCTA)_3$ TA $(TCTA)_3$ TCA $(TCTA)_2$ TCCATA $(TCTA)_{12}$ TA TCTA TCGTCT;
$(TCTA)_5$ $(TCTG)_6$ $(TCTA)_3$ TA $(TCTA)_3$ TCA $(TCTA)_2$ TCCATA $(TCTA)_{13}$ TA TCTA TCGTCT;
$(TCTA)_5$ $(TCTG)_6$ $(TCTA)_3$ TA $(TCTA)_3$ TCA $(TCTA)_2$ TCCATA $(TCTA)_{14}$ TATCTA TCGTCT;
$(TCTA)_{10}$ $(TCTG)_5$ $(TCTA)_3$ TA $(TCTA)_3$ TCA $(TCTA)_2$ TCCATA $(TCTA)_{12}$ TCGTCT;
$(TCTA)_{11}$ $(TCTG)_5$ $(TCTA)_3$ TA $(TCTA)_3$ TCA $(TCTA)_2$ TCCATA $(TCTA)_{12}$ TCGTCT;
$(TCTA)_{11}$ $(TCTG)_5$ $(TCTA)_3$ TA $(TCTA)_3$ TCA $(TCTA)_2$ TCCATA $(TCTA)_{13}$ TCGTCT; or
$(TCTA)_{13}$ $(TCTG)_5$ $(TCTA)_3$ TA $(TCTA)_3$ TCA $(TCTA)_2$ TCCATA $(TCTA)_{12}$ TCGTCT; or at least 75% homologous thereto;

vi) an allelic ladder for locus D18S51 comprising an allele comprising or consisting of sequence:
$(AGAA)_8$; or at least 75% homologous thereto.

Preferably the mixture includes allelic ladders for a plurality of loci. It is particularly preferred that the mixture include allelic ladders for at least four loci. Preferably the mixture includes allelic ladders for a plurality of loci selected from HUMVWFA31/A, HUMTHO1, D8S1179, HUMFIBRA/FGA, D21S11 and D18S51. Preferably the mixture includes allelic ladders for at least four of these loci. In its most preferred form the mixture includes allelic ladders for all of these loci.

Preferably the mixture includes an amelogenin sex test.

Preferably one or more of the allelic ladders in the mixture includes at least 7 alleles and more preferably at least 12 alleles. Preferably a plurality, and particularly all, the allelic ladders of the mixture include at least 8 and more preferably at least 10 alleles.

Preferably one or more or all of the ladders, if present in the mixture may be provided such that: the HUMVWFA31/A allelic ladder includes at least 9, more preferably 11 and ideally 12 alleles; the HUMTHO1 allelic ladder includes at least 7, more preferably 9 and ideally 10 alleles; the D8S1179 allelic ladder includes at least 9, more preferably 12 and ideally 13 alleles; the HUMFIBRA/FGA allelic ladder includes at least 18, more preferably 26 and ideally 28 alleles or is present as HUMFIBRA/FGA/LW and HUMFIBRA/FGA/HW with the HUMFIBRA/FGA/LW ladder including at least 16 more preferably 18 and ideally 20 alleles, the HUMFIBRA/FGA/HW ladder including at least 6, more preferably at leats 7 and ideally 8 alleles; the D21S11 allelic ladder includes at least 14, more preferably 16 and ideally 17 alleles; and the D18S51 ladder includes at least 15, more preferably 19 and ideally 20 alleles.

Preferably one or more of the allelic ladders in the mixture comprises at least 4 pairs of alleles 4 base pairs from each other. More preferably at least 10 pairs, and ideally at least 12 pairs of alleles are so provided. Preferably one or more or all the allelic ladders, if present in the mixture, may be provided such that: the HUMVWFA31/A allelic ladder includes at least 7, more preferably 10 and ideally 11 pairs of alleles 4 base pairs from each other; the HUMTHO1 allelic ladder includes at least 5, more preferably 6 and ideally 7 pairs of alleles 4 base pairs from each other; the D8S1179 allelic ladder includes at least 8, more preferably 11 and ideally 12 pairs of alleles 4 base pairs from each other; the HUMFIBRA/FGA allelic ladder includes at least 17, more preferably 20 and ideally 23 pairs of alleles 4 base pairs from each other; the D21S11 allelic ladder includes at least 3 and ideally 4 pairs of alleles 4 base pairs from each other; and the D18S51 ladder includes at least 13, more preferably 18 and ideally 19 pairs of alleles 4 base pairs from each other. The D21S11 allelic ladder may, or may further include, at least 8, more preferably 11 and ideally 12 pairs of alleles 8 base pairs from each other.

Preferably the allele sequences have at least 85% homogeneity with the listed sequences More preferable levels of even 90% or at least 95% may be provided. Ideally the exact sequences listed are included within the alleles. In their most preferred form the alleles consist of the listed sequences.

The alleles may further include flanking sequences, ie. between the primer and STR.

Preferably the HUMVWFA31/A ladder includes alleles ranging from 130, more preferably 126 and ideally 122 base pairs upwards and/or from 166 base pairs downwards. Preferably the HUMTHO1 ladder includes alleles ranging from 150 base pairs upwards and/or 189 base pairs downwards. Preferably the D8S1179 ladder includes alleles ranging from 157 base pairs upwards and/or 201, and more preferably 205 base pairs downwards. Preferably the HUMFIBRA/FGA ladder includes alleles ranging from 173 base pairs upwards and/or 298, more preferably 302 and ideally 310 base pairs downwards. Preferably the D21S11 ladder includes alleles ranging from 203 base pairs upwards and/or 255 or more preferably 259 base pairs downwards. Preferably the D18S51 ladder includes alleles ranging from 270 or more preferably 266 base pairs upwards and/or 326 or 330 or 334 or 338 or even 342 downwards.

According to a second aspect of the invention we provide an allelic ladder mixture comprising an allelic ladder for one or more of the following loci, with lowest molecular weight allele and/or uppermost molecular weight allele as follows:

|   | Locus | Lowest Designation | Highest Designation |
|---|---|---|---|
| a) | HUMVWFA31/A | 10 | 21 |
| b) | HUMTH01 | 4 | 13.3 |
| c) | D8S1179 | 7 | 19 |
| d) | HUMFIBRA/FGA | 16.1 | 50.2 |
| e) | D21S11 | 53 | 81 |
| f) | D18S51 | 8 | 27 |

Preferably one or more of the loci ladders have both the upper and lower limits specified. Preferably all the loci ladders have the full ranges listed.

Preferably the mixture includes allelic ladders for a plurality of loci. It is particularly preferred that the mixture include allelic ladders for at least four loci. Preferably the mixture includes allelic ladders for a plurality of loci selected from HUMVWFA31/A, HUMTHO1, D8S1179, HUMFIBRA/FGA, D21S11 and D18S51. Preferably the mixture includes allelic ladders for at least four of these loci. In its most preferred form the mixture includes allelic ladders for all of these loci.

The intervals of alleles in the ladders and/or number of alleles in the ladders may be as specified in the first aspect of the invention. This aspect may include any of the other features specified elsewhere in the application.

The ladder mixtures of the first and/or second aspect of the invention may further include one or more of PARR buffer, primer(s), or Taq polymerase.

According to a third aspect of the invention we provide a method of analysing one or more samples comprising:
 a) obtaining genomic DNA from the sample;
 b) amplifying the DNA;
 c) obtaining an indication of one or more of the constituent parts of the sample; and comparing the indications with an allelic ladder mixture comprising one or more of the following allelic ladders:
  i) an allelic ladder for locus HUMVWFA31/A comprising one or more of alleles comprising or consisting of sequences:
   TCTA TCTG TCTA $(TCTG)_4$ $(TCTA)_3$;
   TCTA $(TCTG)_4$ $(TCTA)_7$; or
   $(TCTA)_2$ $(TCTG)_4$ $(TCTA)_3$ TCCA $(TCTA)_3$
  ii) an allelic ladder for locus HUMTHO1 comprising or consisting of sequence:
   $(TCAT)_4$ CAT $(TCAT)_7$ TCGT TCAT;
  iii) an allelic ladder for locus D8S1179 comprising one or more of alleles comprising or consisting of sequences:
   $(TCTA)_8$; or
   $(TCTA)_2$ TCTG $(TCTA)_{16}$;
  iv) an allelic ladder for locus HUMFIBRA/FGA comprising one or more of alleles comprising or consisting of the sequences:

(TTTC)$_3$ TTTT TTCT (CTTT)$_5$ T (CTTT)$_3$ CTCC (TTCC)$_2$;
(TTTC)$_3$ TTTT TTCT (CTTT)$_{13}$ CCTT (CTTT)$_5$ CTCC (TTCC)$_2$;
(TTTC)$_3$ TTTT TTCT (CTTT)$_{16}$ CCTT (CTTT)$_5$ CTCC (TTCC)$_2$;
(TTTC)$_4$ TTTT TT (CTTT)$_{15}$ (CTTC)$_3$ (CTTT)$_3$ CTCC (TTCC)$_4$;
(TTTC)$_4$ TTTT TT (CTTT)$_{16}$ (CTTC)$_3$ (CTTT)$_3$ CTCC (TTCC)$_4$;
(TTTC)$_4$ TTTT TT (CTTT)$_{17}$ (CTTC)$_3$ (CTTT)$_3$ CTCC (TTCC)$_4$;
(TTTC)$_4$ TTTT TT (CTTT)$_8$ (CTGT)$_4$ (CTTT)$_{13}$ (CTTC)$_4$ (CTTT)$_3$ CTCC (TTCC)$_4$;
(TTTC)$_4$ TTTT TT (CTTT)$_8$ (CTGT)$_5$ (CTTT)$_{13}$ (CTTC)$_4$ (CTTT)$_3$ CTCC (TTCC)$_4$;
(TTTC)$_4$ TTTT TT (CTTT)$_{11}$ (CTGT)$_3$ (CTTT)$_{14}$ (CTTC)$_3$ (CTTT)$_3$ CTCC (TTCC)$_4$;
(TTTC)$_4$ TTTT TT (CTTT)$_{10}$ (CTGT)$_5$ (CTTT)$_{13}$ (CTTC)$_4$ (CTTT)$_3$ CTCC (TTCC)$_4$;
(TTTC)$_4$ TTTT TT (CTTT)$_{12}$ (CTGT)$_5$ (CTTT)$_{14}$ (CTTC)$_3$ (CTTT)$_3$ CTCC (TTCC)$_4$; or
(TTTC)$_4$ TTTT TT (CTTT)$_{14}$ (CTGT)$_3$ (CTTT)$_{14}$ (CTTC)$_4$ (CTTT)$_3$ CTCC (TTCC)$_4$;

v) an allelic ladder for locus D21S11 comprising one or more of alleles comprising or consisting of sequences:
(TCTA)$_4$ (TCTG)$_6$ (TCTA)$_3$ TA(TCTA)$_3$ TCA (TCTA)$_2$ TCCATA (TCTA)$_6$ TCGTCT;
(TCTA)$_5$ (TCTG)$_6$ (TCTA)$_3$ TCA (TCTA)$_2$ TCCATA (TCTA)$_9$ TCGTCT;
(TCTA)$_5$ (TCTG)$_6$ (TCTA)$_3$ TCA (TCTA)$_2$ TCCATA (TCTA)$_{10}$ TCGTCT;
(TCTA)$_4$ (TCTG)$_6$ (TCTA)$_3$ TA (TCTA)$_3$ TCA (TCTA)$_2$ TCCATA (TCTA)$_8$ TCGTCT;
(TCTA)$_5$ (TCTG)$_5$ (TCTA)$_3$ TA (TCTA)$_3$ TCA (TCTA)$_2$ TCCATA (TCTA)$_9$ TCGTCT;
(TCTA)$_4$ (TCTG)$_6$ (TCTA)$_3$ TA (TCTA)$_3$ TCA (TCTA)$_2$ TCCATA (TCTA)$_{10}$ TCGTCT;
(TCTA)$_4$ (TCTG)$_6$ (TCTA)$_3$ TA (TCTA)$_3$ TCA (TCTA)$_2$ TCCATA (TCTA)$_{11}$ TCGTCT;
(TCTA)$_6$ (TCTG)$_5$ (TCTA)$_3$ TA (TCTA)$_3$ TCA (TCTA)$_2$ TCCATA (TCTA)$_{11}$ TCGTCT;
(TCTA)$_5$ (TCTG)$_6$ (TCTA)$_3$ TA (TCTA)$_3$ TCA (TCTA)$_2$ TCCATA (TCTA)$_{12}$ TCGTCT;
(TCTA)$_5$ (TCTG)$_6$ (TCTA)$_3$ TA (TCTA)$_3$ TCA (TCTA)$_2$ TCCATA (TCTA)$_{11}$ TA TCTA TCGTCT;
(TCTA)$_5$ (TCTG)$_6$ (TCTA)$_3$ TA (TCTA)$_3$ TCA (TCTA)$_2$ TCCATA (TCTA)$_{12}$ TA TCTA TCGTCT;
(TCTA)$_5$ (TCTG)$_6$ (TCTA)$_3$ TA (TCTA)$_3$ TCA (TCTA)$_2$ TCCATA (TCTA)$_{13}$ TA TCTA TCGTCT;
(TCTA)$_5$ (TCTG)$_6$ (TCTA)$_3$ TA (TCTA)$_3$ TCA (TCTA)$_2$ TCCATA (TCTA)$_{14}$ TATCTA TCGTCT;
(TCTA)$_{10}$ (TCTG)$_5$ (TCTA)$_3$ TA (TCTA)$_3$ TCA (TCTA)$_2$ TCCATA (TCTA)$_{12}$ TCGTCT;
(TCTA)$_{11}$ (TCTG)$_5$ (TCTA)$_3$ TA (TCTA)$_3$ TCA (TCTA)$_2$ TCCATA (TCTA)$_{12}$ TCGTCT;
(TCTA)$_{11}$ (TCTG)$_5$ (TCTA)$_3$ TA (TCTA)$_3$ TCA (TCTA)$_2$ TCCATA (TCTA)$_{13}$ TCGTCT; or
(TCTA)$_{13}$ (TCTG)$_5$ (TCTA)$_3$ TA (TCTA)$_3$ TCA (TCTA)$_2$ TCCATA (TCTA)$_{12}$ TCGTCT;

vi) an allelic ladder for locus D18S51 comprising an allele comprising or consisting of sequence:
(AGAA)$_8$;

including allelic ladders or alleles 75% homologous thereto.

The allelic ladder mixture may possess other features specified in the first or second aspects of the invention or elsewhere in this application.

Preferably the DNA sample is one or more of a sample taken from the scene of a crime, a sample associated with the scene of a crime, a sample obtained from a suspect, a sample obtained from a human under consideration (for instance for paternity or maternity analysis) or a reference sample. The sample may be in the form of blood, hair, skin or bodily fluid.

Preferably the sample is amplified using a polymerase chain reaction. Preferably primers for one or more of loci HUMVWFA31/A, HUMTHO1, D8S1179, HUMFIBRA/FGA, D21S11 or D18S51 are employed. The primers may be dye or otherwise labelled.

According to a fourth aspect of the invention we provide one or more alleles comprising or consisting of sequences
TCTA TCTG TCTA (TCTG)$_4$ (TCTA)$_3$;
TCTA (TCTG)$_4$ (TCTA)$_7$;
(TCTA)$_2$ (TCTG)$_4$ (TCTA)$_3$ TCCA (TCTA)$_3$;
(TCAT)$_4$ CAT (TCAT)$_7$ TCGT TCAT;
(TCTA)$_8$;
(TCTA)$_2$ TCTG (TCTA)$_{16}$;
(TTTC)$_3$ TTTT TTCT (CTTT)$_5$ T (CTTT)$_3$ CTCC (TTCC)$_2$;
(TTTC)$_3$ TTTT TTCT (CTTT)$_{13}$ CCTT (CTTT)$_5$ CTCC (TTCC)$_2$;
(TTTC)$_3$ TTTT TTCT (CTTT)$_{16}$ CCTT (CTTT)$_5$ CTCC (TTCC)$_2$;
(TTTC)$_4$ TTTT TT (CTTT)$_{15}$ (CTTC)$_3$ (CTTT)$_3$ CTCC (TTCC)$_4$;
(TTTC)$_4$ TTTT TT (CTTT)$_{16}$ (CTTC)$_3$ (CTTT)$_3$ CTCC (TTCC)$_4$;
(TTTC)$_4$ TTTT TT (CTTT)$_{17}$ (CTTC)$_3$ (CTTT)$_3$ CTCC (TTCC)$_4$;
(TTTC)$_4$ TTTT TT (CTTT)$_8$ (CTGT)$_4$ (CTTT)$_{13}$ (CTTC)$_4$ (CTTT)$_3$ CTCC (TTCC)$_4$;
(TTTC)$_4$ TTTT TT (CTTT)$_8$ (CTGT)$_5$ (CTTT)$_{13}$ (CTTC)$_4$ (CTTT)$_3$ CTCC (TTCC)$_4$;
(TTTC)$_4$ TTTT TT (CTTT)$_{11}$ (CTGT)$_3$ (CTTT)$_{14}$ (CTTC)$_3$ (CTTT)$_3$ CTCC (TTCC)$_4$;
(TTTC)$_4$ TTTT TT (CTTT)$_{10}$ (CTGT)$_5$ (CTTT)$_{13}$ (CTTC)$_4$ (CTTT)$_3$ CTCC (TTCC)$_4$;
(TTTC)$_4$ TTTT TT (CTTT)$_{12}$ (CTGT)$_5$ (CTTT)$_{14}$ (CTTC)$_3$ (CTTT)$_3$ CTCC (TTCC)$_4$;
(TTTC)$_4$ TTTT TT (CTTT)$_{14}$ (CTGT)$_3$ (CTTT)$_{14}$ (CTTC)$_4$ (CTTT)$_2$ CTCC (TTCC)$_4$;
(TCTA)$_4$ (TCTG)$_6$ (TCTA)$_3$ TA(TCTA)$_3$ TCA (TCTA)$_2$ TCCATA (TCTA)$_6$ TCGTCT;
(TCTA)$_5$ (TCTG)$_6$ (TCTA)$_3$ TCA (TCTA)$_2$ TCCATA (TCTA)$_9$ TCGTCT;
(TCTA)$_5$ (TCTG)$_6$ (TCTA)$_3$ TCA (TCTA)$_2$ TCCATA (TCTA)$_{10}$ TCGTCT;
(TCTA)$_4$ (TCTG)$_6$ (TCTA)$_3$ TA (TCTA)$_3$ TCA (TCTA)$_2$ TCCATA (TCTA)$_8$ TCGTCT;
(TCTA)$_5$ (TCTG)$_5$ (TCTA)$_3$ TA (TCTA)$_3$ TCA (TCTA)$_2$ TCCATA (TCTA)$_9$ TCGTCT;
(TCTA)$_4$ (TCTG)$_6$ (TCTA)$_3$ TA (TCTA)$_3$ TCA (TCTA)$_2$ TCCATA (TCTA)$_{10}$ TCGTCT;
(TCTA)$_4$ (TCTG)$_6$ (TCTA)$_3$ TA (TCTA)$_3$ TCA (TCTA)$_2$ TCCATA (TCTA)$_{11}$ TCGTCT;
(TCTA)$_6$ (TCTG)$_5$ (TCTA)$_3$ TA (TCTA)$_3$ TCA (TCTA)$_2$ TCCATA (TCTA)$_{11}$ TCGTCT;
(TCTA)$_5$ (TCTG)$_6$ (TCTA)$_3$ TA (TCTA)$_3$ TCA (TCTA)$_2$ TCCATA (TCTA)$_{12}$ TCGTCT;
(TCTA)$_5$ (TCTG)$_6$ (TCTA)$_3$ TA (TCTA)$_3$ TCA (TCTA)$_2$ TCCATA (TCTA)$_{11}$ TA TCTA TCGTCT;

(TCTA)$_5$ (TCTG)$_6$ (TCTA)$_3$ TA (TCTA)$_3$ TCA (TCTA)$_2$ TCCATA (TCTA)$_{12}$ TA TCTA TCGTCT;
(TCTA)$_5$ (TCTG)$_6$ (TCTA)$_3$ TA (TCTA)$_3$ TCA (TCTA)$_2$ TCCATA (TCTA)$_{13}$ TA TCTA TCGTCT;
(TCTA)$_5$ (TCTG)$_6$ (TCTA)$_3$ TA (TCTA)$_3$ TCA (TCTA)$_2$ TCCATA (TCTA)$_{14}$ TATCTA TCGTCT;
(TCTA)$_{10}$ (TCTG)$_5$ (TCTA)$_3$ TA (TCTA)$_3$ TCA (TCTA)$_2$ TCCATA (TCTA)$_{12}$ TCGTCT;
(TCTA)$_{11}$ (TCTG)$_5$ (TCTA)$_3$ TA (TCTA)$_3$ TCA (TCTA)$_2$ TCCATA (TCTA)$_{12}$ TCGTCT;
(TCTA)$_{11}$ (TCTG)$_5$ (TCTA)$_3$ TA (TCTA)$_3$ TCA (TCTA)$_2$ TCCATA (TCTA)$_{13}$ TCGTCT;
(TCTA)$_{13}$ (TCTG)$_5$ (TCTA)$_3$ TA (TCTA)$_3$ TCA (TCTA)$_2$ TCCATA (TCTA)$_{12}$ TCGTCT; or
(AGAA)$_8$; or at least 75% homologous thereto.

Preferably the alleles are provided purified from alleles other than those of HUMVWFA31/A, HUMTH01, D8S1179, HUMFIBRA/FGA, D21511, D18551 or AMG loci.

According to a fifth aspect of the invention we provide the use of an allelic ladder according to the first aspect of the invention and/or an allele according to the fourth aspect of the invention for comparison with a DNA analysis result.

The analysis may be a DNA profile of a sample. The profile may be based on analysis of one or more loci, in particular including one or more of HUMVWFA31/A, HUMTH01, D8S1179, HUMFIBRA/FGA, D21S11, D18S51 or AMG. The sample may be from the scene of a crime, associated with the scene of a crime or comprise a bodily fluid sample. The sample may be used to compare two or more individuals, or samples arising therefrom, for instance in paternity and/or maternity analysis.

According to a sixth aspect of the invention we provide a method of producing an allelic ladder or mixture thereof by subjecting the ladders of the first, second or fourth aspects of the invention to PCR.

The invention will now be described, by way of example only, and with reference to the accompanying figure in which:

FIG. 1 illustrates the locus, allele designation and size for an embodiment of the invention;

FIG. 3a shows the sequence of selected alleles forming the HUMVWFA31/A ladder;

FIG. 3b shows the sequence of selected alleles forming the HUMTH01 ladder;

FIG. 3c shows the sequence of selected alleles forming the D8S1179 ladder;

FIG. 3d shows the sequence of selected alleles forming the HUMFIBRA ladder;

FIG. 3e shows the sequence of selected alleles forming the D21S11 ladder; and

FIG. 3f shows the sequence of selected alleles forming the D18S51 ladder.

An allelic ladder mixture illustrative of the present invention is provided for loci HUMTHO1, D21S11, D8S1179, HUMVWFA31/A, HUMFIBRA/FGA and amelogenin sex test. The loci nomenclature is standard, corresponding to that used in the GENEBANK database.

The ladder mixture includes a significant number of alleles for each locus so as to provide a base line for comparison across a wide range. The loci, allelic designation and base pair sizes for the mixture are shown in FIG. 1. The nomenclature for the loci is discussed in Gill et al. 1996 *Int. Journal Leg. Med.* 109 14–22.

The allelic ladder mixture was presented in PARR buffer (containing Tris and 1.5 mM Mg ions at pH8.0) obtained from Cambio, primers obtained from Oswell and Taq polymerase from Perkin Elmer.

Figure 2A:
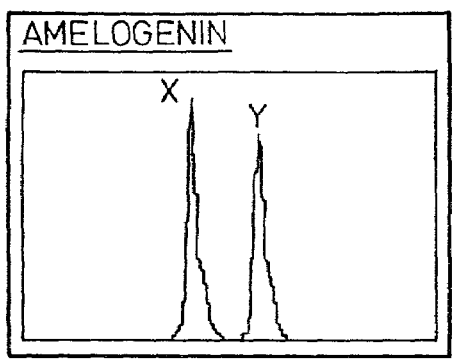
FIG. 2a shows an electrophoretogram of the allelic ladder for Amelogenin (AMG)
Figure 2B:
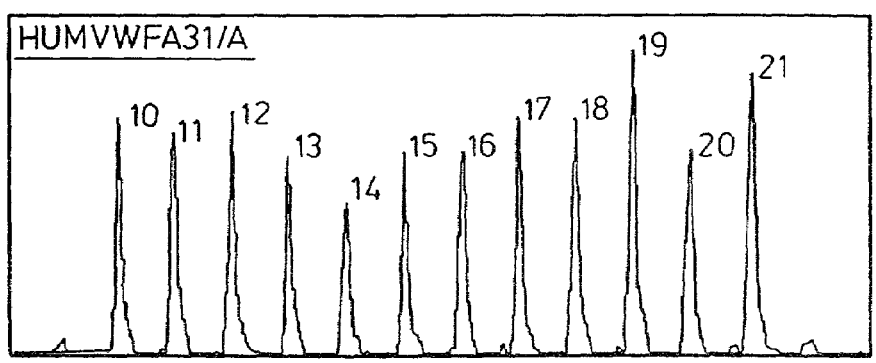
FIG. 2b shows an electrophoretogram of the allelic ladder for HUMVWFA31/A.
Figure 2C:
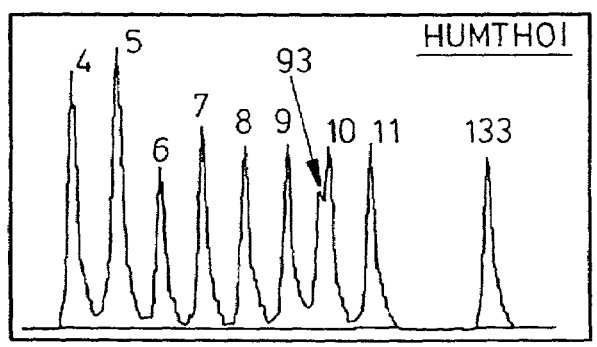
FIG. 2c shows an electrophoretogram of the allelic ladder for HUMTH01.
Figure 2D:
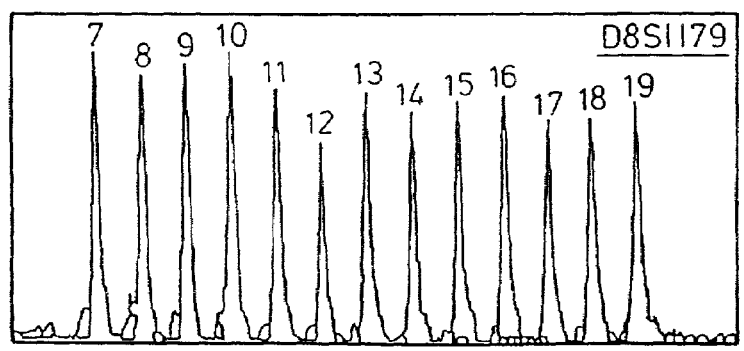
FIG. 2d shows an electrophoretogram of the allelic ladder for D8S1179.
Figure 2E:
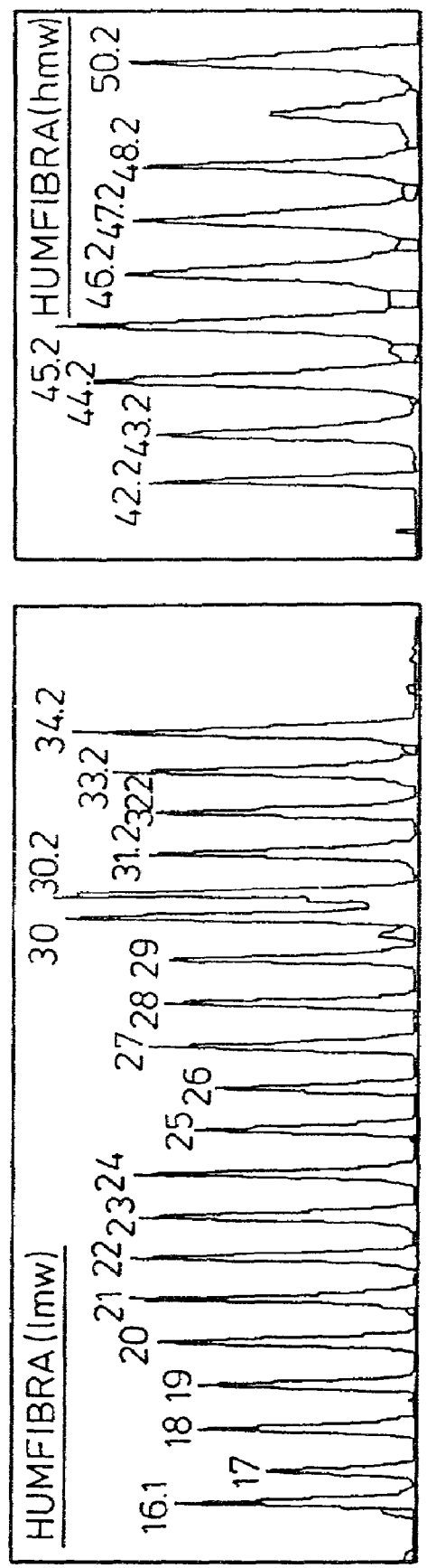
FIG. 2e shows an electrophoretogram or the allelic ladder for HUMFIBRA, low and high molecular weights.
Figure 2F:
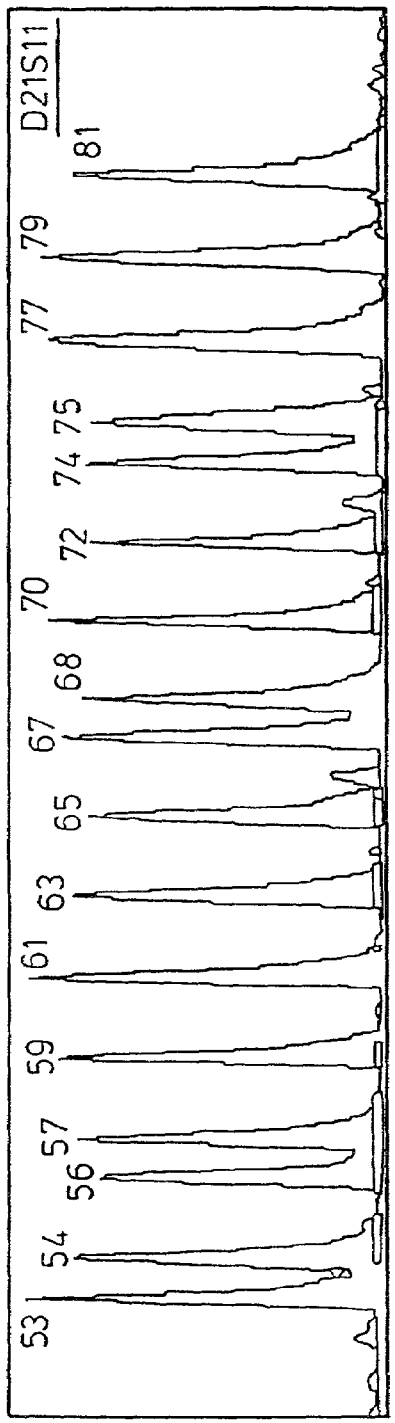
FIG. 2f shows an electrophoretogram of the allelic ladder for D21S11.
Figure 2G:
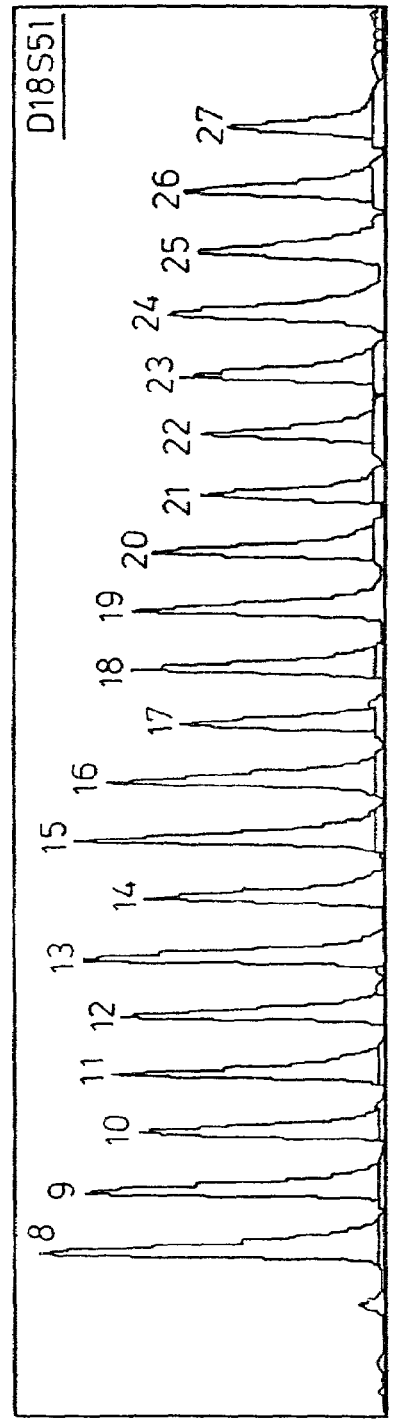
FIG. 2g shows an electrophoretogram of the allelic ladder for D18S51.

Electrophoretograms for the allelic ladders are shown in FIGS. 2a to 2g with the allelic number designations shown.

FIGS. 3a to 3f show the sequences for the alleles identified in FIGS. 2a to 2g.

The allelic ladder mixture discussed above was produced according to the following techniques. Buccal swabs and/or bloodstains were used as the sample sources. The genomic DNA was extracted using the chelex procedure described by Walsh et al. 1991 *Bio. Techniques* 1 91–98.

The recovered DNA was quantified by dot hybridisation using a higher primate specific probe, as disclosed in Walsh et al. 1992 *Nucleic Acids Res.* 20 5061–5065.

Each sample was then amplified according to the conditions set out below in Table 1 with unlabelled oligonucleotide primers, the sequences for which are disclosed in Urquhart et al. 1995 *Bio Techniques* 18 116–121 and Oldroyd et al. 1995 *Electrophoresis* 16 334–337.

TABLE 1

| D18 | 95° C. for 60 seconds | D21 | 94° C. for 30 seconds |
| --- | --- | --- | --- |
|  | 60° C. for 60 seconds |  | 58° C. for 60 seconds |
|  | 72° C. for 60 seconds |  | 72° C. for 30 seconds |
| Method: 28 cycles + 72° C. for 10 minutes then hold at 4° C. | | Method: 26 cycles + 72° C. for 10 minutes then hold at 4° C. | |
| D8 | 94° C. for 30 seconds | TH01 | 94° C. for 45 seconds |
|  | 60° C. for 60 seconds | and | 60° C. for 60 seconds |
|  | 72° C. for 60 seconds | VWA | 72° C. for 60 seconds |
| Method: 30 cycles + 72° C. for 10 minutes then hold at 4° C. | | Method: 28 cycles + 72° C. for 10 minutes then hold at 4° C. | |
| FGA | 93° C. for 60 seconds | Amelo | 93° C. for 30 seconds |
|  | 60° C. for 60 seconds |  | 58° C. for 75 seconds |
|  | 72° C. for 60 seconds |  | 72° C. for 15 seconds |
| Method: 30 cycles + 72° C. for 10 minutes then hold at 4° C. | | Method: 30 cycles + 72° C. for 10 minutes then hold at 4° C. | |

Individual alleles were then isolated and sequence analysis was carried out according to the methods of Barber et al. 1996 *Int. Journal Leg. Med.* 108 180–185 and Barber and Parkin 1996 *Int. Journal Leg. Med.* 109 62–65. Both DNA strands of each allele reported were sequenced and the sequences provided in FIGS. 3a to 3g are the consensus results for this.

The illustrations of the alleles provided in FIGS. 3a to 3g follow the nomenclature recommended by the DNA commission of the International Society of Forensic Haemogenetics 1994 *Int. Journal Leg. Med.* 107 159–160 where the complete number of tandem repeats observed are designated by the digit. The longhand version of these sequences is provided at the end of the specific description.

To prepare the ladder cocktail amplification of the alleles is necessary. This process was performed by amplifying the purified single alleles described above using a labelled primer in each case. For the locus HUMFIBRA/FGA the ladder was produced from two separate mixes, discussed in more detail below. The primers used are disclosed in Urquhart et al. 1995 *Bio Techniques* 18 116–121 and Oldroyd et al. 1995 *Electrophoresis* 16 334–337 and were employed according to the conditions set out above in Table 1.

The singleplexs produced in this way were analysed on an Applied Biosystems 377 automated sequencer to confirm the sequences. The sequences obtained from the profiling system are one base longer than those determined form the DNA sequencing technique initially discussed above. This is due to the ability of DNA polymerase from *Thermus aquaticus* to catalyse a non-template mediated addition of a deoxyribonucleotide to the 3' hydroxyl of PCR products. This is generally known as the "n+1" product and can be generated in preference to the "n" product. The results reported here, however, refer to the "n" product rather than the "n+1" product for which the labelled primer PCR conditions have been optimised to produce.

The products of the amplification process for each locus were then diluted, mixed with one another and reanalysed to produce a single ladder for each loci having even peak heights. An initial level of 1000 Arbitary Units, AU, was increased to 1000–5000 AU to give greater signal strength and volume for the ladder.

The single ladders produced in this way were then mixed together to give the cocktail discussed above. The proportions of each ladder used are controlled to give balanced peak areas. The cocktail was then validated using Applied Biosystems 373A and Applied Biosystems 377 automated sequencers with Genescan and Genotyper software.

Allelic ladders according to the invention can be prepared by applying PCR amplification techniques to a pre-existing sample of the allelic ladder mixture. Alternatively the allelic ladders can be constructed from the sequence information provided herein.

The new ladders disclosed above significantly extends the range of alleles which can be identified in any DNA profiling system. The allelic ladder mixture is used as a control sample alongside samples from known or unknown individuals which are then segregated according to size in a gel. Alleles in the sample under test can be designated by the known alleles in the control if they are within 0.5 bases of one another. Alleles falling outside this range are estimated based on their position relative to the ladder.

Using the standard nomenclature discussed above, the ladder range for each locus, defined by the extreme low molecular weight and extreme high molecular weight alleles are:

| Locus | Low MW allele | High MW allele |
|---|---|---|
| HUMVWFA31/A | 10 | 21 |
| HUMTH01 | 4 | 13.3 |
| D8S1179 | 7 | 19 |
| HUMFIBRA/FGA | 16.1 | 50.2 |
| D21S11 | 53 | 81 |
| D18S51 | 8 | 27 |

The allelic ladders also enables the identification of certain rare and hence highly discriminatory alleles, in DNA profiling thus increasing the profiling systems power.

For the various locus certain alleles are of particular significance as follows:

Locus HUMTHO1

The primers used for this locus were labelled with 6-FAM. The polymorphic region of this locus is based around a tetranucleotide motif repeat, $(TCAT)_n$, where n=4 to 13. Particular alleles provided by the present invention include 4, 9.3, 10 and 13.3. The 9.3 and 13.3 alleles were found to have a deletion of a thiamine nucleotide at either the last base of the 4th repeat unit or the first base of the 5th repeat unit. The 13.3 allele notably possesses a non-consensus tetranucleotide (TCGT) at the 13th repeat.

Locus D21S11

The primers for this locus were also labelled with 6-FAM. The allele range extends from 53 to 81 and significantly includes alleles 53, 56, 57, 79 and 81. The polymorphic region of the D21S11 alleles is relatively complex in structure and is based around the tetranucleotide TCTR, where R is A or G (following the ambiguity codes of the Nomenclature Committee of the International Union of Biochemistry), as well as containing invariant hexa-, tri- and di-nucleotides. Both allele 54 and allele 56 deviate from this general structure in that they possess a deletion of a 14 base pair $TA(TCTA)_3$ unit immediately prior to the invariant TCA tetranucleotide.

Locus D18S51

Again primers with a 6-FAM label were used. The ladder extends to 20 distinct alleles with particularly significant alleles at 8, 9, 23, 24, 25, 26 and 27. The polymorphic region is based around a simple tetranucleotide repeat motif $(AGAA)_n$, where n is 8 to 27.

Locus D8S1179

The primers used for this locus were labelled with TET. The ladder extends from alleles 7 to 19, based on 13 separate alleles. Significant alleles include 7, 15, 18 and 19. Different generalised structures were observed between the upper and lower molecular weight ends of the ladder. In the lower molecular weight area, 161 to 177 base pairs, a simple repeat region based on the tetranucleotide TCTA exists. In the higher weight region, 181 to 201 base pairs, a compound repeat region composed of the tetranucleotide TCTR was found.

Locus HUMVWFA31/A

HEX labelled primers were used for this locus. The ladder covers alleles between 10 and 21, based on 12 alleles in total. Noteworthy alleles 10, 11 and 12 are included. The polymorphic unit is generally composed of a compound repeat following the pattern $(TCTR)_n$. For the 13 and 14 alleles a non-consensus TCCA tetranucleotide at the 10th and 11th repeats was found.

Locus HUMFIBRA/FGA

This locus also employed HEX labelled primers. As mentioned above this ladder was constructed in two separate components. A low molecular weight and high molecular weight mix was used to produce the overall ladder. The low molecular weight mix ranges from allele 16.1 to 34.2 and the high molecular weight mix from allele 42.2 to 50.2.

The low MW mix includes significant alleles 16.1, 28, 30, 30.2, 31.2, 32.2, 33.2 and 34.2. The high MW mix includes noteworthy alleles 42.2, 43.2, 44.2, 45.2, 47.2, 48.2 and 50.2.

In general the HUMFIBRA/FGA alleles have a polymorphic unit based around the compound repeat YYBY, with the alleles in the upper part of the weight range being more complex in structure than those in the lower part. Within the general framework, allele 16.1 has a T nucleotide addition in the repeat region and allele 27 has a C to T transition in the 19th repeat unit (CTTT to CCTT). The upper MW allele range includes a stutter peak which is 4 base pairs smaller than the 50.2 allele. This artifact corresponds to allele 49.2 which has not currently been determined.

Amelogenin

Primers for this locus were once again labelled with 6-FAM. The sequence data revealed an X specific product of 105 base pairs and a Y specific product of 111 base pairs.

```
HUMTH01 allele sequences 13.3   (TCAT)4 CAT (TCAT)7 TCGT TCAT

D21S11 alleles sequences 53     (TCTA)4 (TCTG)6 (TCTA)3 TA (TCTA)3 TCA (TCTA)2 TCCATA (TCTA)6 TCGTCT 54     (TCTA)5 (TCTG)6 (TCTA)3 TCA (TCTA)2 TCCATA (TCTA)9 TCGTCT 56     (TCTA)5 (TCTG)6 (TCTA)3 TCA (TCTA)2 TCCATA (TCTA)10 TCGTCT 57     (TCTA)4 (TCTG)6 (TCTA)3 TA (TCTA)3 TCA (TCTA)2 TCCATA (TCTA)8 TCGTCT 59     (TCTA)5 (TCTG)5 (TCTA)3 TA (TCTA)3 TCA (TCTA)2 TCCATA (TCTA)9 TCGTCT 61     (TCTA)4 (TCTG)6 (TCTA)3 TA (TCTA)3 TCA (TCTA)2 TCCATA (TCTA)10 TCGTCT 63     (TCTA)4 (TCTG)6 (TCTA)3 TA (TCTA)3 TCA (TCTA)2 TCCATA (TCTA)11 TCGTCT 65     (TCTA)6 (TCTG)5 (TCTA)3 TA (TCTA)3 TCA (TCTA)2 TCCATA (TCTA)11 TCGTCT 67     (TCTA)5 (TCTG)6 (TCTA)3 TA (TCTA)3 TCA (TCTA)2 TCCATA (TCTA)12 TCGTCT 68     (TCTA)5 (TCTG)6 (TCTA)3 TA (TCTA)3 TCA (TCTA)2 TCCATA (TCTA)11 TA TCTA TCGTCT 70     (TCTA)5 (TCTG)6 (TCTA)3 TA (TCTA)3 TCA (TCTA)2 TCCATA (TCTA)12 TA TCTA TCGTCT 72     (TCTA)5 (TCTG)6 (TCTA)3 TA (TCTA)3 TCA (TCTA)2 TCCATA (TCTA)13 TA TCTA TCGTCT 74     (TCTA)5 (TCTG)6 (TCTA)3 TA (TCTA)3 TCA (TCTA)2 TCCATA (TCTA)14 TATCTA TCGTCT 75     (TCTA)10 (TCTG)5 (TCTA)3 TA (TCTA)3 TCA (TCTA)2 TCCATA (TCTA)12 TCGTCT 77     (TCTA)11 (TCTG)5 (TCTA)3 TA (TCTA)3 TCA (TCTA)2 TCCATA (TCTA)12 TCGTCT 79     (TCTA)11 (TCTG)5 (TCTA)3 TA (TCTA)3 TCA (TCTA)2 TCCATA (TCTA)13 TCGTCT 81     (TCTA)13 (TCTG)5 (TCTA)3 TA (TCTA)3 TCA (TCTA)2 TCCATA (TCTA)12 TCGTCT D18S51 allele sequences 8      (AGAA)8

D8S1179 allele sequences 7      (TCTA)8

19     (TCTA)2 TCTG (TCTA)16

HUMVWAF31/A allele sequences

10     TCTA TCTG TCTA (TCTG)4 (TCTA)3

12     TCTA (TCTG)4 (TCTA)7

13     (TCTA)2 (TCTG)4 (TCTA)3 TCCA (TCTA)3

(Note also that the allele has an atypical 3' flanking sequence. The usual sequence is
TCCA TCTA T. In this allele the sequence is (TCCA)2T.

HUMFIBRA (FGA) allele sequences 16.1   (TTTC)3 TTTT TTCT (CTTT)5 T (CTTT)3 CTCC (TTCC)2

27     (TTTC)3 TTTT TTCT (CTTT)13 CCTT (CTTT)5 CTCC (TTCC)2

30     (TTTC)3 TTTT TTCT (CTTT)16 CCTT (CTTT)5 CTCC (TTCC)2

31.2   (TTTC)4 TTTT TT (CTTT)15 (CTTC)3 (CTTT)3 CTCC (TTCC)4

32.2   (TTTC)4 TTTT TT (CTTT)16 (CTTC)3 (CTTT)3 CTCC (TTCC)4
```

-continued 33.2 (TTTC)$_4$ TTTT TT (CTTT)$_{17}$ (CTTC)$_3$ (CTTT)$_3$ CTCC (TTCC)$_4$ 42.2 (TTTC)$_4$ TTTT TT (CTTT)$_8$ (CTGT)$_4$ (CTTT)$_{13}$ (CTTC)$_4$ (CTTT)$_3$ CTCC (TTCC)$_4$ 43.2 (TTTC)$_4$ TTTT TT (CTTT)$_8$ (CTGT)$_5$ (CTTT)$_{13}$ (CTTC)$_4$ (CTTT)$_3$ CTCC (TTCC)$_4$ 44.2 (TTTC)$_4$ TTTT TT (CTTT)$_{11}$ (CTGT)$_3$ (CTTT)$_{14}$ (CTTC)$_3$ (CTTT)$_3$ CTCC (TTCC)$_4$ 45.2 (TTTC)$_4$ TTTT TT (CTTT)$_{10}$ (CTGT)$_5$ (CTTT)$_{13}$ (CTTC)$_4$ (CTTT)$_3$ CTCC (TTCC)$_4$ 47.2 (TTTC)$_4$ TTTT TT (CTTT)$_{12}$ (CTGT)$_5$ (CTTT)$_{14}$ (CTTC)$_3$ (CTTT)$_3$ CTCC (TTCC)$_4$ 48.2 (TTTC)$_4$ TTTT TT (CTTT)$_{14}$ (CTGT)$_3$ (CTTT)$_{14}$ (CTTC)$_4$ (CTTT)$_3$ CTCC (TTCC)$_4$

---

The invention claimed is:

1. An allelic ladder mixture comprising one or more of the following allelic ladders:

i) an allelic ladder for locus HUMVWFA31/A comprising one or more alleles with a short tandem repeat sequence consisting of sequences:

TCTA TCTG TCTA $(TCTG)_4$ $(TCTA)_3$ —SEQ ID NO 1; or

TCTA $(TCTG)_4$ $(TCTA)_7$ —SEQ ID NO 2; or $(TCTA)_2$ $(TCTG)_4$ $(TCTA)_3$ TCCA $(TCTA)_3$ —SEQ ID NO 3;

ii) an allelic ladder for locus HUMTHO1 comprising an allele with a short tandem repeat sequence consisting of sequence:

$(TCAT)_4$ CAT $(TCAT)_7$ TCGT TCAT —SEQ ID NO 4;

iii) an allelic ladder for locus D85 1179 comprising an allele with a short tandem repeat sequence consisting of sequence:

$(TCTA)_2$ TCTG$(TCTA)_{16}$ —SEQ ID NO 6;

iv) an allelic ladder for locus HUMFIBRA/FGA comprising one or more alleles with a short tandem repeat sequence consisting of sequences:

$(TTTC)_3$ TTTT TTCT $(CTTT)_5$ T $(CTTT)_3$ CTCC $(TTCC)_2$ —SEQ ID NO 7; or $(TTTC)_3$ TTTT TTCT $(CTTT)_{13}$ CCTT $(CTTT)_5$ CTCC $(TTCC)_2$ —SEQ ID NO 8; or $(TTTC)_3$ TTTT TTCT $(CTTT)_{16}$ CCTT $(CTTT)_5$ CTCC $(TTCC)_2$ —SEQ IID NO 9; or $(TTTC)_4$ TTTT TT $(CTTT)_{15}$ $(CTTC)_3$ $(CTTT)_3$ CTCC $(TTCC)_4$ —SEQ ID NO 10; or $(TTTC)_4$ TTTT TT $(CTTT)_{16}$ $(CTTC)_3$ $(CTTT)_3$ CTCC $(TTCC)_4$ —SEQ IID NO 11; or $(TTTC)_4$ TTTT TT $(CTTT)_{17}$ $(CTTC)_3$ $(CTTT)_3$ CTCC $(TTCC)_4$ —SEQ ID NO 12; or $(TTTC)_4$ TTTT TT $(CTTT)_8$ $(CTGT)_4$ $(CTTT)_{13}$ $(CTTC)_4$ $(CTTT)_3$ CTCC $(TTCC)_4$ —SEQ ID NO 13; or $(TTTC)_4$ TTTT TT $(CTTT)_8$ $(CTGT)_5$ $(CTTT)_{13}$ $(CTTC)_4$ $(CTTT)_3$ CTCC $(TTCC)_4$ —SEQ ID NO 14; or $(TTTC)_4$ TTTT TT $(CTTT)_{11}$ $(CTGT)_3$ $(CTTT)_{14}$ $(CTTC)_3$ $(CTTT)_3$ CTCC $(TTCC)_4$ —SEQ ID NO 15; or $(TTTC)_4$ TTTT TT $(CTTT)_{10}$ $(CTGT)_5$ $(CTTT)_{13}$ $(CTTC)_4$ $(CTTT)_3$ CTCC $(TTCC)_4$ —SEQ ID NO 16; or $(TTTC)_4$ TTTT TT $(CTTT)_{12}$ $(CTGT)_5$ $(CTTT)_{14}$ $(CTTC)_3$ $(CTTT)_3$ CTCC $(TTCC)_4$ —SEQ ID NO 17; or $(TTTC)_4$ TTTT TT $(CTTT)_{14}$ $(CTGT)_3$ $(CTTT)_{14}$ $(CTTC)_4$ $(CTTT)_3$ CTCC $(TTCC)_4$ —SEQ ID NO 18;

v) an allelic ladder for locus D21S11 comprising one or more alleles with a short tandem repeat sequence consisting of sequences:

$(TCTA)_4$ $(TCTG)_6$ $(TCTA)_3$ TA$(TCTA)_3$ TCA $(TCTA)_2$ TCCATA $(TCTA)_6$ TCGTCT —SEQ ID NO 19; or $(TCTA)_5$ $(TCTG)_6$ $(TCTA)_3$ TCA $(TCTA)_2$ TCCATA $(TCTA)_9$ TCGTCT —SEQ ID NO 20 or $(TCTA)_5$ $(TCTG)_6$ $(TCTA)_3$ TCA $(TCTA)_2$ TCCATA $(TCTA)_{10}$ TCGTCT —SEQ ID NO 21; or $(TCTA)_4$ $(TCTG)_6$ $(TCTA)_3$ TA $(TCTA)_3$ TCA $(TCTA)_2$ TCCATA $(TCTA)_8$ TCGTCT —SEQ ID NO 22; or $(TCTA)_5$ $(TCTG)_5$ $(TCTA)_3$ TA $(TCTA)_3$ TCA $(TCTA)_2$ TCCATA $(TCTA)_9$ TCGTCT —SEQ ID NO 23; or $(TCTA)_4$ $(TCTG)_6$ $(TCTA)_3$ TA $(TCTA)_3$ TCA $(TCTA)_2$ TCCATA $(TCTA)_{10}$ TCGTCT —SEQ ID NO 24; or $(TCTA)_4$ $(TCTG)_6$ $(TCTA)_3$ TA $(TCTA)_3$ TCA $(TCTA)_2$ TCCATA $(TCTA)_{11}$ TCGTCT —SEQ ID NO 25; or $(TCTA)_6$ $(TCTG)_5$ $(TCTA)_3$ TA $(TCTA)_3$ TCA $(TCTA)_2$ TCCATA $(TCTA)_{11}$ TCGTCT —SEQ ID NO 26; or $(TCTA)_5$ $(TCTG)_6$ $(TCTA)_3$ TA $(TCTA)_3$ TCA $(TCTA)_2$ TCCATA $(TCTA)_{12}$ TCGTCT —SEQ ID NO 27; or $(TCTA)_5$ $(TCTG)_6$ $(TCTA)_3$ TA $(TCTA)_3$ TCA $(TCTA)_2$ TCCATA $(TCTA)_{11}$ TA TCTA TCGTCT —SEQ ID NO 28; or $(TCTA)_5$ $(TCTG)_6$ $(TCTA)_3$ TA $(TCTA)_3$ TCA $(TCTA)_2$ TCCATA $(TCTA)_{12}$ TA TCTA TCGTCT —SEQ ID NO 29; or $(TCTA)_5$ $(TCTG)_6$ $(TCTA)_3$ TA $(TCTA)_3$ TCA $(TCTA)_2$ TCCATA $(TCTA)_{13}$ TA TCTA TCGTCT —SEQ ID NO 30; or (TCTA)$_5$ (TCTG)$_6$ (TCTA)$_3$ TA (TCTA)$_3$ TCA (TCTA)$_2$ TCCATA (TCTA)$_{14}$ TATCTA TCGTCT —SEQ ID NO 31; or (TCTA)$_{10}$ (TCTG)$_5$ (TCTA)$_3$ TA (TCTA)$_3$ TCA (TCTA)$_2$ TCCATA (TCTA)$_{12}$ TCGTCT —SEQ ID NO 32; or (TCTA)$_{11}$ (TCTG)$_5$ (TCTA)$_3$ TA (TCTA)$_3$ TCA (TCTA)$_2$ TCCATA (TCTA)$_{12}$ TCGTCT —SEQ ID NO 33; or (TCTA)$_{11}$ (TCTG)$_5$ (TCTA)$_3$ TA (TCTA)$_3$ TCA (TCTA)$_2$ TCCATA (TCTA)$_{13}$ TCGTCT —SEQ ID NO 34; or (TCTA)$_{13}$ (TCTG)$_5$ (TCTA)$_3$ TA (TCTA)$_3$ TCA (TCTA)$_2$ TCCATA (TCTA)$_{12}$ TCGTCT —SEQ ID NO 35;

vi) an allelic ladder for locus D18S51 comprising an allele with a short tandem repeat sequence consisting of sequence:

(AGAA)$_8$ —SEQ ID NO 36.

2. An allelic ladder mixture according to claim 1 in which the mixture includes allelic ladders for a plurality of loci selected from HUMVWFA31/A, HUMTHO1, D8S1179, HUMFIBRA/FGA, D21S11 and D18S51.

3. An allelic ladder mixture according to claim 1 the mixture including allelic ladders for at least four loci.

4. An allelic ladder mixture according to claim 1 in which the allelic ladders in the mixture each include at least 7 alleles.

5. An allelic ladder mixture according to claim 1 in which the ladders, if present in the mixture, are provided such that: the HUMVWFA31/A allelic ladder includes at least 9 alleles;

the HUMTHO1 allelic ladder includes at least 7; the D8S1179 allelic ladder includes at least 9 alleles; the HUMFIIBRA/FGA allelic ladder includes at least 18 alleles or is present as HUMFIBRA/FGA/LW and HUMFIBRA/FGA/HW with the HUMFIBRA/FGA/LW ladder including at least 16 alleles, the HUMFIBRA/FGA/HW ladder including at least 6 alleles; the D21S11 allelic ladder includes at least 14 alleles; and the D18S51 ladder includes at least 15 alleles.

6. An allelic ladder mixture according to claim 1 in which one or more of the allelic ladders in the mixture comprises at least 4 pairs of alleles 4 base pairs from each other.

7. An allelic ladder mixture according to claim 1 in which the ladders, if present in the mixture, are provided such that: the HUMVWFA31/A allelic ladder includes at least 7 pairs of alleles 4 base pairs from each other; the HUMTHO1 allelic ladder includes at least 5 pairs of alleles 4 base pairs from each other; the D8S1179 allelic ladder includes at least 8 pairs of alleles 4 base pairs from each other; the HUMFIBRA/FGA allelic ladder includes at least 17 pairs of alleles 4 base pairs from each other; the D21S11 allelic ladder includes at least 3 pairs of alleles 4 base pairs from each other; and the D18S51 ladder includes at least 13 pairs of alleles 4 base pairs from each other.

8. An allelic ladder mixture according to claim 7 in which the D21S11 allelic ladder includes at least 8 pairs of alleles 8 base pairs from each other.

9. An allelic ladder mixture according to claim 1 in which the ladders, if present, are provided such that the HUMVWFA31/A ladder includes alleles ranging from 130 base pairs upwards and/or from 166 base pairs downwards; the HUMTHO1 ladder includes alleles ranging from 150 base pairs upwards and/or 189 base pairs downwards; the D8S1179 ladder includes alleles ranging from 157 base pairs upwards and/or 201 base pairs downwards; the HUMFIBRA/FGA ladder includes alleles ranging from 173 base pairs upwards and/or 298 base pairs downwards; the D21S11 ladder includes alleles ranging from 203 base pairs upwards and/or 255 base pairs downwards; and the D18S51 ladder includes alleles ranging from 270 base pairs upwards and/or 326 downwards.

10. An allelic ladder mixture comprising an allelic ladder for one or more of the following loci, with lowest and highest allele designation as follows:

| | Locus | Low MW allele | High MW allele |
|---|---|---|---|
| a) | HUMVWFA31/A | 10 | 21 |
| b) | HUMTH01 | 4 | 13.3 |
| c) | D8S1179 | 7 | 19 |
| d) | HUMFIBRA/FGA | 16.1 | 50.2 |
| e) | D21S11 | 53 | 81 |
| f) | D18S51 | 8 | 27. |

11. An allelic ladder mixture according to claim 10 in which the mixture includes allelic ladders for loci HUMVWFA31/A, HUMTHO1, D8S1179, HUMFIBRA/FGA, D21S11 and D18S51.

12. A method of analysing one or more samples comprising:

a) obtaining genomic DNA from the sample;

b) amplifying the DNA;

c) obtaining an indication of one or more of the constituent parts of the sample;

and comparing the indications with an allelic ladder mixture comprising one or more of the following allelic ladders:

i) an allelic ladder for locus TUMVWFA31/A comprising one or more alleles with a short tandem repeat sequence consisting of sequences:

TCTA TCTG TCTA (TCTG)$_4$ (TCTA)$_3$ —SEQ ID NO 1; or

TCTA (TCTG)$_4$ (TCTA)$_7$ —SEQ ID NO 2; or (TCTA)$_2$ (TCTG)$_4$ (TCTA)$_3$ TCCA (TCTA)$_3$ —SEQ ID NO 3 ii) an allelic ladder for locus HUMTHO1 comprising an allele with a short tandem repeat sequence consisting of sequence:

(TCAT)$_4$ CAT (TCAT)$_7$ TCGT TCAT —SEQ ID NO 4;

iii) an allelic ladder for locus D8S1179 comprising an allele with a short tandem repeat sequence consisting of sequence:

(TCTA)$_2$ TCTG (TCTA)$_{16}$ —SEQ ID NO 6;

iv) an allelic ladder for locus HUMFIBRA/FGA comprising one or more alleles with a short tandem repeat sequence consisting of the sequences:

(TTTC)$_3$ TTTT TTCT (CTTT)$_5$ T (CTTT)$_3$ CTCC (TTCC)$_2$ —SEQ ID NO 7; or (TTTC)$_3$ TTTT TTCT (CTTT)$_{13}$ CCTT (CTTT)$_5$ CTCC (TTCC)$_2$ —SEQ ID NO 8; or (TTTC)$_3$ TTTT TTCT (CTTT)$_{16}$ CCTT (CTTT)$_5$ CTCC (TTCC)$_2$ —SEQ ID NO 9; or (TTTC)$_4$ TTTT TT (CTTT)$_{15}$ (CTTC)$_3$ (CTTT)$_3$ CTCC (TTCC)$_4$ —SEQ ID NO 10; or (TTTC)$_4$ TTTT TT (CTTT)$_{16}$ (CTTC)$_3$ (CTTT)$_3$ CTCC (TTCC)$_4$ —SEQ ID NO 11; or (TTTC)$_4$ TTTT TT (CTTT)$_{17}$ (CTTC)$_3$ (CTTT)$_3$ CTCC (TTCC)$_4$ —SEQ ID NO 12; or (TTTC)$_4$ TTTT TT (CTTT)$_8$ (CTGT)$_4$ (CTTT)$_{13}$ (CTTC)$_4$ (CTTT)$_3$ CTCC (TTCC)$_4$ —SEQ ID NO 13; or (TTTC)$_4$ TTTT TT (CTTT)$_8$ (CTGT)$_5$ (CTTT)$_{13}$ (CTTC)$_4$ (CTTT)$_3$ CTCC (TTCC)$_4$ —SEQ ID NO 14; or (TTTC)$_4$ TTTT TT (CTTT)$_{11}$ (CTGT)$_3$ (CTTT)$_{14}$ (CTTC)$_3$ (CTTT)$_3$ CTCC (TTCC)$_4$ —SEQ IID NO 15; or (TTTC)$_4$ TTTT TT (CTTT)$_{10}$ (CTGT)$_5$ (CTTT)$_{13}$ (CTTC)$_4$ (CTTT)$_3$ CTCC (TTCC)$_4$ —SEQ ID NO 16; or (TTTC)$_4$ TTTT TT (CTTT)$_{12}$ (CTGT)$_5$ (CTTT)$_{14}$ (CTTC)$_3$ (CTTT)$_3$ CTCC (TTCC)$_4$ —SEQ ID NO 17; or (TTTC)$_4$ TTTT TT (CTTT)$_{14}$ (CTGT)$_3$ (CTTT)$_{14}$ (CTTC)$_4$ (CTTT)$_3$ CTCC (TTCC)$_4$ —SEQ ID NO 18;

v) an allelic ladder for locus D21S11 comprising one or more alleles with a short tandem repeat sequence consisting of sequences:

(TCTA)$_4$ (TCTG)$_6$ (TCTA)$_3$ TA(TCTA)$_3$ TCA (TCTA)$_2$ TCCATA (TCTA)$_6$ TCGTCT —SEQ ID NO 19; or (TCTA)$_5$ (TCTG)$_6$ (TCTA)$_3$ TCA (TCTA)$_2$ TCCATA (TCTA)$_9$ TCGTCT —SEQ ID NO 20; or (TCTA)$_5$ (TCTG)$_6$ (TCTA)$_3$ TCA (TCTA)$_2$ TCCATA (TCTA)$_{10}$ TCGTCT—SEQ ID NO 21; or (TCTA)$_4$ (TCTG)$_6$ (TCTA)$_3$ TA (TCTA)$_3$ TCA (TCTA)$_2$ TCCATA (TCTA)$_8$ TCGTCT —SEQ ID NO 22; or (TCTA)$_5$ (TCTG)$_5$ (TCTA)$_3$ TA (TCTA)$_3$ TCA (TCTA)$_2$ TCCATA (TCTA)$_9$ TCGTCT —SEQ ID NO 23; or (TCTA)$_4$ (TCTG)$_6$ (TCTA)$_3$ TA (TCTA)$_3$ TCA (TCTA)$_2$ TCCATA (TCTA)$_{10}$ TCGTCT —SEQ ID NO 24; or (TCTA)$_4$ (TCTG)$_6$ (TCTA)$_3$ TA (TCTA)$_3$ TCA (TCTA)$_2$ TCCATA (TCTA)$_{11}$ TCGTCT —SEQ ID NO 25; or (TCTA)$_6$ (TCTG)$_5$ (TCTA)$_3$ TA (TCTA)$_3$ TCA (TCTA)$_2$ TCCATA (TCTA)$_{11}$ TCGTCT —SEQ ID NO 26; or (TCTA)$_5$ (TCTG)$_6$ (TCTA)$_3$ TA (TCTA)$_3$ TCA (TCTA)$_2$ TCCATA (TCTA)$_{12}$ TCGTCT —SEQ ID NO 27; or (TCTA)$_5$ (TCTG)$_6$ (TCTA)$_3$ TA (TCTA)$_3$ TCA (TCTA)$_2$ TCCATA (TCTA)$_{11}$ TA TCTA TCGTCT —SEQ ID NO 28; or (TCTA)$_5$ (TCTG)$_6$ (TCTA)$_3$ TA (TCTA)$_3$ TCA (TCTA)$_2$ TCCATA (TCTA)$_{12}$ TA TCTA TCGTCT —SEQ ID NO 29; or (TCTA)$_5$ (TCTG)$_6$ (TCTA)$_3$ TA (TCTA)$_3$ TCA (TCTA)$_2$ TCCATA (TCTA)$_{13}$ TA TCTA TCGTCT —SEQ ID NO 30; or (TCTA)$_5$ (TCTG)$_6$ (TCTA)$_3$ TA (TCTA)$_3$ TCA (TCTA)$_2$ TCCATA (TCTA)$_{14}$ TATCTA TCGTCT —SEQ ID NO 31; or (TCTA)$_{10}$ (TCTG)$_5$ (TCTA)$_3$ TA (TCTA)$_3$ TCA (TCTA)$_2$ TCCATA (TCTA)$_{12}$ TCGTCT —SEQ ID NO 32; or (TCTA)$_{11}$ (TCTG)$_5$ (TCTA)$_3$ TA (TCTA)$_3$ TCA (TCTA)$_2$ TCCATA (TCTA)$_{12}$ TCGTCT —SEQ ID NO 33; or (TCTA)$_{11}$ (TCTG)$_5$ (TCTA)$_3$ TA (TCTA)$_3$ TCA (TCTA)$_2$ TCCATA (TCTA)$_{13}$ TCGTCT —SEQ ID NO 34; or (TCTA)$_{13}$ (TCTG)$_5$ (TCTA)$_3$ TA (TCTA)$_3$ TCA (TCTA)$_2$ TCCATA (TCTA)$_{12}$ TCGTCT —SEQ ID NO 35;

vi) an allelic ladder for locus D18S51 comprising an allele with a short tandem repeat sequence consisting of sequence:

(AGAA)$_8$ —SEQ ID NO 36.

13. A method according to claim 12 in which the DNA sample is one or more of a sample taken from the scene of a crime, a sample associated with the scene of a crime, a sample obtained from a suspect, a sample obtained from a human under consideration or a reference sample.

14. A method according to claim 12 in which the sample is amplified using a polymerase chain reaction and primers for one or more of loci HUMVWFA31/A, HUMTHO1, D8S1179, HUMFIBRA/FGA, D21S11 or D18S51 are employed.

15. An allelic ladder mixture comprising one or more of the following allelic ladders:

i) an allelic ladder for locus HIJMVWFA31/A comprising one or more alleles having a flanking sequence on either side of a sequence consisting of sequences:

TCTA TCTG TCTA (TCTG)$_4$ (TCTA)$_3$ —SEQ ID NO 1; or

TCTA (TCTG)$_4$ (TCTA)$_7$ —SEQ ID NO 2; or (TCTA)$_2$ (TCTG)$_4$ (TCTA)$_3$ TCCA (TCTA)$_3$ —SEQ ID NO 3;

ii) an allelic ladder for locus HUMTHO1 comprising an allele having a flanking sequence on either side of a sequence consisting of sequence:

(TCAT)$_4$ CAT (TCAT)$_7$ TCGT TCAT —SEQ ID NO 4;

iii) an allelic ladder for locus D8S1179 comprising an allele having a flanking sequence on either side of a sequence consisting of sequence:

(TCTA)$_2$ TCTG(TCTA)$_{16}$ —SEQ ID NO 6;

iv) an allelic ladder for locus HUMFIBRA/FGA comprising one or more alleles having a flanking sequence on either side of a sequence consisting of sequences:

(TTTC)$_3$ TTTT TTCT (CTTT)$_5$ T (CTTT)$_3$ CTCC (TTCC)$_2$ —SEQ ID NO 7; or (TTTC)$_3$ TTTT TTCT (CTTT)$_{13}$ CCTT (CTTT)$_5$ CTCC (TTCC)$_2$ —SEQ ID NO 8; or (TTTC)$_3$ TTTT TTCT (CTTT)$_{16}$ CCTT (CTTT)$_5$ CTCC (TTCC)$_2$ —SEQ ID NO 9; or (TTTC)$_4$ TTTT TT (CTTT)$_{15}$ (CTTC)$_3$ (CTTT)$_3$ CTCC (TTCC)$_4$ —SEQ ID NO 10; or (TTTC)$_4$ TTTT TT (CTTT)$_{16}$ (CTTC)$_3$ (CTTT)$_3$ CTCC (TTCC)$_4$ —SEQ ID NO 11; or (TTTC)$_4$ TTTT TT (CTTT)$_{17}$ (CTTC)$_3$ (CTTT)$_3$ CTCC (TTCC)$_4$ —SEQ ID NO 12; or (TTTC)$_4$ TTTT TT (CTTT)$_8$ (CTGT)$_4$ (CTTT)$_{13}$ (CTTC)$_4$ (CTTT)$_3$ CTCC (TTCC)$_4$ —SEQ ID NO 13; or (TTTC)$_4$ TTTT TT (CTTT)$_8$ (CTGT)$_5$ (CTTT)$_{13}$ (CTTC)$_4$ (CTTT)$_3$ CTCC (TTCC)$_4$ —SEQ ID NO 14; or (TTTC)$_4$ TTTT TT (CTTT)$_{11}$ (CTGT)$_3$ (CTTT)$_{14}$ (CTTC)$_3$ (CTTT)$_3$ CTCC (TTCC)$_4$ —SEQ ID NO 15; or (TTTC)$_4$ TTTT TT (CTTT)$_{10}$ (CTGT)$_5$ (CTTT)$_{13}$ (CTTC)$_4$ (CTTT)$_3$ CTCC (TTCC)$_4$ —SEQ ID NO 16; or (TTTC)$_4$ TTTT TT (CTTT)$_{12}$ (CTGT)$_5$ (CTTT)$_{14}$ (CTTC)$_3$ (CTTT)$_3$ CTCC (TTCC)$_4$ —SEQ ID NO 17; or (TTTC)₄ TTTT TT (CTTT)₁₄ (CTGT)₃ (CTTT)₁₄ (CTTC)₄ (CTTT)₃ CTCC (TTCC)₄ —SEQ ID NO 18;

v) an allelic ladder for locus D21S11 comprising one or more alleles having a flanking sequence on either side of a sequence consisting of sequences:
(TCTA)₄ (TCTG)₆ (TCTA)₃ TA(TCTA)₃ TCA (TCTA)₂ TCCATA (TCTA)₆ TCGTCT —SEQ ID NO 19; or
(TCTA)₅ (TCTG)₆ (TCTA)₃ TCA (TCTA)₂ TCCATA (TCTA)₉ TCGTCT —SEQ ID NO 20 or
(TCTA)₅ (TCTG)₆ (TCTA)₃ TCA (TCTA)₂ TCCATA (TCTA)₁₀ TCGTCT—SEQ ID NO 21; or
(TCTA)₄ (TCTG)₆ (TCTA)₃ TA (TCTA)₃ TCA (TCTA)₂ TCCATA (TCTA)₈ TCGTCT —SEQ ID NO 22; or
(TCTA)₅ (TCTG)₅ (TCTA)₃ TA (TCTA)₃ TCA (TCTA)₂ TCCATA (TCTA)₉ TCGTCT —SEQ ID NO 23; or
(TCTA)₄ (TCTG)₆ (TCTA)₃ TA (TCTA)₃ TCA (TCTA)₂ TCCATA (TCTA)₁₀ TCGTCT —SEQ ID NO 24; or
(TCTA)₄ (TCTG)₆ (TCTA)₃ TA (TCTA)₃ TCA (TCTA)₂ TCCATA (TCTA)₁₁ TCGTCT —SEQ ID NO 25; or
(TCTA)₆ (TCTG)₅ (TCTA)₃ TA (TCTA)₃ TCA (TCTA)₂ TCCATA (TCTA)₁₁ TCGTCT —SEQ ID NO 26; or
(TCTA)₅ (TCTG)₆ (TCTA)₃ TA (TCTA)₃ TCA (TCTA)₂ TCCATA (TCTA)₁₂ TCGTCT —SEQ ID NO 27; or
(TCTA)₅ (TCTG)₆ (TCTA)₃ TA (TCTA)₃ TCA (TCTA)₂ TCCATA (TCTA)₁₁ TA TCTA TCGTCT —SEQ ID NO 28; or
(TCTA)₅ (TCTG)₆ (TCTA)₃ TA (TCTA)₃ TCA (TCTA)₂ TCCATA (TCTA)₁₂ TA TCTA TCGTCT —SEQ ID NO 29; or
(TCTA)₅ (TCTG)₆ (TCTA)₃ TA (TCTA)₃ TCA (TCTA)₂ TCCATA (TCTA)₁₃ TA TCTA TCGTCT —SEQ ID NO 30; or
(TCTA)₅ (TCTG)₆ (TCTA)₃ TA (TCTA)₃ TCA (TCTA)₂ TCCATA (TCTA)₁₄ TATCTA TCGTCT —SEQ ID NO 31; or
(TCTA)₁₀ (TCTG)₅ (TCTA)₃ TA (TCTA)₃ TCA (TCTA)₂ TCCATA (TCTA)₁₂ TCGTCT —SEQ ID NO 32; or
(TCTA)₁₁ (TCTG)₅ (TCTA)₃ TA (TCTA)₃ TCA (TCTA)₂ TCCATA (TCTA)₁₂ TCGTCT —SEQ ID NO 33; or
(TCTA)₁₁ (TCTG)₅ (TCTA)₃ TA (TCTA)₃ TCA (TCTA)₂ TCCATA (TCTA)₁₃ TCGTCT —SEQ ID NO 34; or
(TCTA)₁₃ (TCTG)₅ (TCTA)₃ TA (TCTA)₃ TCA (TCTA)₂ TCCATA (TCTA)₁₂ TCGTCT —SEQ ID NO 35;

vi) an allelic ladder for locus D18S51 comprising an allele having a flanking sequence on either side of a sequence consisting of sequence:
(AGAA)₈ —SEQ ID NO 36.

16. An allelic ladder mixture according to claim 15 in which the mixture includes allelic ladders for a plurality of loci selected from HUMVWFA31/A, HUMTHO1, D8S1179, HUMFIBRA/FGA, D21S11 and D18S51.

17. An allelic ladder mixture according to claim 15 the mixture including allelic ladders for at least four loci.

18. An allelic ladder mixture according to claim 15 in which the allelic ladders in the mixture each include at least 7 alleles.

19. An allelic ladder mixture according to claim 15 in which the ladders, if present in the mixture, are provided such that: the HUMVWFA31/A allelic ladder includes at least 9 alleles; the HUMTHO1 allelic ladder includes at least 7; the D8S1179 allelic ladder includes at least 9 alleles; the HUMFIBRA/FGA allelic ladder includes at least 18 alleles or is present as HUMFIBRA/FGA/LW and HUMFIBRA/FGA/HW with the HUMFIBRA/FGA/LW ladder including at least 16 alleles, the HUMFIBRA/FGA/HW ladder including at least 6 alleles; the D21S11 allelic ladder includes at least 14 alleles; and the D18S51 ladder includes at least 15 alleles.

20. An allelic ladder mixture according to claim 15 in which one or more of the allelic ladders in the mixture comprises at least 4 pairs of alleles 4 base pairs from each other.

21. An allelic ladder mixture according to claim 15 in which the ladders, if present in the mixture, are provided such that: the HUMVWFA31/A allelic ladder includes at least 7 pairs of alleles 4 base pairs from each other; the HUMTHO1 allelic ladder includes at least 5 pairs of alleles 4 base pairs from each other; the D8S1179 allelic ladder includes at least 8 pairs of alleles 4 base pairs from each other; the HUMFIBRA/FGA allelic ladder includes at least 17 pairs of alleles 4 base pairs from each other; the D21S11 allelic ladder includes at least 3 pairs of alleles 4 base pairs from each other; and the D18S51 ladder includes at least 13 pairs of alleles 4 base pairs from each other.

22. An allelic ladder mixture according to claim 21 in which the D21S11 allelic ladder includes at least 8 pairs of alleles 8 base pairs from each other.

23. An allelic ladder mixture according to claim 15 in which the ladders, if present, are provided such that the HUMVWFA31/A ladder includes alleles ranging from 130 base pairs upwards and/or from 166 base pairs downwards; the HUMTHO1 ladder includes alleles ranging from 150 base pairs upwards and/or 189 base pairs downwards; the D8S1179 ladder includes alleles ranging from 157 base pairs upwards and/or 201 base pairs downwards; the HUMFIBRA/FGA ladder includes alleles ranging from 173 base pairs upwards and/or 298 base pairs downwards; the D21S11 ladder includes alleles ranging from 203 base pairs upwards and/or 255 base pairs downwards; and the D18S51 ladder includes alleles ranging from 270 base pairs upwards and/or 326 downwards.

24. A method of analysing one or more samples comprising:
a) obtaining genomic DNA from the sample;
b) amplifying the DNA;
c) obtaining an indication of one or more of the constituent parts of the sample;
and comparing the indications with an allelic ladder mixture comprising one or more of the following allelic ladders:
i) an allelic ladder for locus HUMVWFA31/A comprising one or more alleles having a flanking sequence on either side of a sequence consisting of sequences:
TCTA TCTG TCTA (TCTG)₄ (TCTA)₃ —SEQ ID NO 1; or
TCTA (TCTG)₄ (TCTA)₇ —SEQ ID NO 2; or
(TCTA)₂ (TCTG)₄ (TCTA)₃ TCCA (TCTA)₃ —SEQ ID NO 3
ii) an allelic ladder for locus HUMTHO1 comprising an allele having a flanking sequence on either side of a sequence consisting of sequence:

(TCAT)$_4$ CAT (TCAT)$_7$ TCGT TCAT —SEQ ID NO 4;
iii) an allelic ladder for locus D8S1179 comprising an allele having a flanking sequence on either side of a sequence consisting of sequence:
(TCTA)$_2$ TCTG (TCTA)$_{16}$ —SEQ ID NO 6;
iv) an allelic ladder for locus HUMFIBRA/FGA comprising one or more alleles having a flanking sequence on either side of a sequence consisting of the sequences:
(TTTC)$_3$ TTTT TTCT (CTTT)$_5$ T (CTTT)$_3$ CTCC (TTCC)$_2$ —SEQ ID NO 7; or
(TTTC)$_3$ TTTT TTCT (CTTT)$_{13}$ CCTT (CTTT)$_5$ CTCC (TTCC)$_2$ —SEQ ID NO 8; or
(TTTC)$_3$ TTTT TTCT (CTTT)$_{16}$ CCTT (CTTT)$_5$ CTCC (TTCC)$_2$ —SEQ ID NO 9; or
(TTTC)$_4$ TTTT TT (CTTT)$_{15}$ (CTTC)$_3$ (CTTT)$_3$ CTCC (TTCC)$_4$ —SEQ ID NO 10; or
(TTTC)$_4$ TTTT TT (CTTT)$_{16}$ (CTTC)$_3$ (CuT)$_3$ CTCC (TTCC)$_4$ —SEQ ID NO 11; or
(TTTC)$_4$ TTTT TT (CTTT)$_{17}$ (CTTC)$_3$ (CTTT)$_3$ CTCC (TTCC)$_4$ —SEQ ID NO 12; or
(TTTC)$_4$ TTTT TT (CTTT)$_8$ (CTGT)$_4$ (CTTT)$_{13}$ (CTTC)$_4$ (CTTT)$_3$ CTCC (TTCC)$_4$ —SEQ ID NO 13; or
(TTTC)$_4$ TTTT TT (CTTT)$_8$ (CTGT)$_5$ (CTTT)$_{13}$ (CTTC)$_4$ (CTTT)$_3$ CTCC (TTCC)$_4$ —SEQ ID NO 14; or
(TTTC)$_4$ TTTT TT (CTTT)$_{11}$ (CTGT)$_3$ (CTTT)$_{14}$ (CTTC)$_3$ (CTTT)$_3$ CTCC (TTCC)$_4$ —SEQ ID NO 15; or
(TTTC)$_4$ TTTT TT (CTTT)$_{10}$ (CTGT)$_5$ (CTTT)$_{13}$ (CTTC)$_4$ (CTTT)$_3$ CTCC (TTCC)$_4$ —SEQ ID NO 16; or
(TTTC)$_4$ TTTT TT (CTTT)$_{12}$ (CTGT)$_5$ (CTTT)$_{14}$ (CTTC)$_3$ (CTTT)$_3$ CTCC (TTCC)$_4$ —SEQ ID NO 17; or
(TTTC)$_4$ TTTT TT (CTTT)$_{14}$ (CTGT)$_3$ (CTTT)$_{14}$ (CTTC)$_4$ (CTTT)$_3$ CTCC (TTCC)$_4$ —SEQ ID NO 18;
v) an allelic ladder for locus D21S11 comprising one or more alleles having a flanking sequence on either side of a sequence consisting of sequences
(TCTA)$_4$ (TCTG)$_6$ (TCTA)$_3$ TA(TCTA)$_3$ TCA (TCTA)$_2$ TCCATA (TCTA)$_6$ TCGTCT —SEQ ID NO 19; or
(TCTA)$_5$ (TCTG)$_6$ (TCTA)$_3$ TCA (TCTA)$_2$ TCCATA (TCTA)$_9$ TCGTCT —SEQ ID NO 20; or
(TCTA)$_5$ (TCTG)$_6$ (TCTA)$_3$ TCA (TCTA)$_2$ TCCATA (TCTA)$_{10}$ TCGTCT —SEQ ID NO 21; or
(TCTA)$_4$ (TCTG)$_6$ (TCTA)$_3$ TA (TCTA)$_3$ TCA (TCTA)$_2$ TCCATA (TCTA)$_8$ TCGTCT —SEQ ID NO 22; or
(TCTA)$_5$ (TCTG)$_5$ (TCTA)$_3$ TA (TCTA)$_3$ TCA (TCTA)$_2$ TCCATA (TCTA)$_9$ TCGTCT —SEQ ID NO 23; or
(TCTA)$_4$ (TCTG)$_6$ (TCTA)$_3$ TA (TCTA)$_3$ TCA (TCTA)$_2$ TCCATA (TCTA)$_{10}$ TCGTCT —SEQ ID NO 24; or
(TCTA)$_4$ (TCTG)$_6$ (TCTA)$_3$ TA (TCTA)$_3$ TCA (TCTA)$_2$ TCCATA (TCTA)$_{11}$ TCGTCT —SEQ ID NO 25; or
(TCTA)$_6$ (TCTG)$_5$ (TCTA)$_3$ TA (TCTA)$_3$ TCA (TCTA)$_2$ TCCATA (TCTA)$_{11}$ TCGTCT —SEQ ID NO 26; or
(TCTA)$_5$ (TCTG)$_6$ (TCTA)$_3$ TA (TCTA)$_3$ TCA (TCTA)$_2$ TCCATA (TCTA)$_{12}$ TCGTCT —SEQ ID NO 27; or
(TCTA)$_5$ (TCTG)$_6$ (TCTA)$_3$ TA (TCTA)$_3$ TCA (TCTA)$_2$ TCCATA (TCTA)$_{11}$ TA TCTA TCGTCT —SEQ ID NO 28; or
(TCTA)$_5$ (TCTG)$_6$ (TCTA)$_3$ TA (TCTA)$_3$ TCA (TCTA)$_2$ TCCATA (TCTA)$_{12}$ TA TCTA TCGTCT —SEQ ID NO 29; or
(TCTA)$_5$ (TCTG)$_6$ (TCTA)$_3$ TA (TCTA)$_3$ TCA (TCTA)$_2$ TCCATA (TCTA)$_{13}$ TA TCTA TCGTCT —SEQ ID NO 30; or
(TCTA)$_5$ (TCTG)$_6$ (TCTA)$_3$ TA (TCTA)$_3$ TCA (TCTA)$_2$ TCCATA (TCTA)$_{14}$ TATCTA TCGTCT —SEQ ID NO 31; or
(TCTA)$_{10}$ (TCTG)$_5$ (TCTA)$_3$ TA (TCTA)$_3$ TCA (TCTA)$_2$ TCCATA (TCTA)$_{12}$ TCGTCT —SEQ ID NO 32; or
(TCTA)$_{11}$ (TCTG)$_5$ (TCTA)$_3$ TA (TCTA)$_3$ TCA (TCTA)$_2$ TCCATA (TCTA)$_{12}$ TCGTCT —SEQ ID NO 33; or
(TCTA)$_{11}$ (TCTG)$_5$ (TCTA)$_3$ TA (TCTA)$_3$ TCA (TCTA)$_2$ TCCATA (TCTA)$_{13}$ TCGTCT —SEQ ID NO 34; or
(TCTA)$_{13}$ (TCTG)$_5$ (TCTA)$_3$ TA (TCTA)$_3$ TCA (TCTA)$_2$ TCCATA (TCTA)$_{12}$ TCGTCT —SEQ ID NO 35;
vi) an allelic ladder for locus D18S51 comprising an allele having a flanking sequence on either side of a sequence consisting of sequence
(AGAA)$_8$ —SEQ ID NO 36.

25. A method according to claim 24 in which the DNA sample is one or more of a sample taken from the scene of a crime, a sample associated with the scene of a crime, a sample obtained from a suspect, a sample obtained from a human under consideration or a reference sample.

26. A method according to claim 24 in which the sample is amplified using a polymerase chain reaction and primers for one or more of loci HUMVWFA31/A, HUMTHO1, D8S1179, HUMFIBRA/FGA, D21S11 or D18S51 are employed.

* * * * *